(12) United States Patent
Flam et al.

(10) Patent No.: US 8,947,374 B2
(45) Date of Patent: Feb. 3, 2015

(54) ELECTRONIC MEDICAL SYSTEM TOUCH PHRASE TECHNOLOGY

(75) Inventors: Seth Flam, San Diego, CA (US); Arnold Mentze, San Marcos, CA (US); Rumpa Giri, Solana Beach, CA (US); Sol Lizerbram, Rancho Santa Fe, CA (US); Jonathan Flam, San Diego, CA (US)

(73) Assignee: HealthFusion, Inc., Solana Beach, CA (US)

( * ) Notice: Subject to any disclaimer, the term of this patent is extended or adjusted under 35 U.S.C. 154(b) by 760 days.

(21) Appl. No.: 13/022,310

(22) Filed: Feb. 7, 2011

(65) Prior Publication Data

US 2012/0200507 A1    Aug. 9, 2012

(51) Int. Cl.
*G06F 3/041* (2006.01)
*G06Q 50/00* (2012.01)
*G06F 19/00* (2011.01)
*G06Q 50/22* (2012.01)

(52) U.S. Cl.
CPC .......... *G06F 19/3487* (2013.01); *G06F 19/322* (2013.01); *G06F 19/3456* (2013.01); *G06F 19/363* (2013.01); *G06Q 50/22* (2013.01)

USPC .............................................. 345/173; 705/2

(58) Field of Classification Search
CPC .............. G06F 19/322; G06F 19/3456; G06F 19/3487; G06F 19/363; G06F 3/0488; G06F 3/0412; G06F 3/0416
USPC ................... 345/173–178; 178/18.01–18.09; 705/2–5
See application file for complete search history.

(56) References Cited

U.S. PATENT DOCUMENTS

| 6,177,940 B1 * | 1/2001 | Bond et al. .................... 434/262 |
| 6,381,577 B1 * | 4/2002 | Brown ............................ 705/2 |
| 7,028,912 B1 * | 4/2006 | Rosen ........................... 236/1 C |
| 2008/0228526 A1 * | 9/2008 | Locke et al. ....................... 705/3 |
| 2008/0231608 A1 * | 9/2008 | Nagata ........................... 345/173 |
| 2012/0004902 A1 * | 1/2012 | Sorkey et al. ..................... 704/9 |

* cited by examiner

*Primary Examiner* — Hong Zhou
(74) *Attorney, Agent, or Firm* — Foley & Lardner LLP

(57) ABSTRACT

Electronic medical system touch phrase technology includes a method comprising initializing a touch phrase button by a processor such that the initializing associates a first text with the touch phrase button; receiving an input associated with the touch phrase button; updating a state of the touch phrase button based upon the input including associating a second text with the touch phrase button; and communicating the state of the touch phrase button to a memory device.

20 Claims, 43 Drawing Sheets

| Chart | Administrative | Allergies | Encounters | Medication List | Problem List | Orders | Family hx |

Neurologic    EDIT_TEST

ENT

Throat
Examination of the pharynx reveals the following: inflammation, exudate located: diffusely this pathology is consistent with: bacterial infection.

Cardiovascular
Upon palpation of the chest wall there are no heaves, lifts, or thrills. The rate is normal, the rhythm is regular, S1 and S2 are normal, there are no murmurs, no gallops, and there are no rubs. There is no pitting edema of the lower extremities. There are no bruits. The peripheral artery pulses are 2+ brisk.

Respiratory
The patient is relaxed and breathes without effort. The patient is not cyanotic and does not use the accessory muscles of respiration. The AP diameter of the chest is normal. The chest expands symmetrically upon inspiration. Upon palpation of the chest wall there is no tenderness or masses. Tactile fremitus is normal and symmetrical. The lungs are clear to percussion. There are no crackles, wheezes, rhonchi, stridor or pleural rubs. There is no bronchophony, egophony, or whispered pectoriloquy.

Gastrointestinal
The abdomen is soft and nontender; there is no guarding or rigidity. Bowel sounds are normal. There are no palpable masses. There is no hepatosplenomegaly. There is no costovertebral angle (CVA) tenderness.

Musculoskeletal

Spine Ribs

Cervical Spine

Osteopathic
There is a somatic dysfunction on the right side. T- Tissue Changes; Tone 2 - Moderate increase in tone right. T- Tissue Changes; Texture 2 - Moderate increase in texture right.

2210

Lymphatics

Cervical
The posterior auricular lymph nodes are palpable bilaterally they are tender.

| Chart | Administrative | Allergies | Encounters | Medication List | Problem List | Orders | Family Hx |
|---|---|---|---|---|---|---|---|

CAGE score is 0   3225

Medical History:

Negative History
The patient's medical history is negative for Cancer, Cholesterol High, Depression, Diabetes, and Thyroid Dz

Positive History

| Condition | Physician | Hospitalization | Hosp Date | Hospital |
|---|---|---|---|---|
| TB | Smith, Randy D.O. | Never | | |

Surgical History:

Negative History
The patient's medical history is negative for Aortic aneurysm, Appendectomy, Augmentation of breast, Reduction of breast, Colectomy, Cholecystectomy, and Cesarean section

Positive History

| Condition | Physician | Hospitalization | Hosp Date | Hospital |
|---|---|---|---|---|
| Abdominal hernia | Jones, Suzanne D.O. | One | 1990 | Dearborn Surgery Center, Llc |

Immunization History:

| Vaccine | Brand Name | Dose | Date Given | Route | Site | Initials |
|---|---|---|---|---|---|---|
| FluLaval 0.5 Vial | Glaxo | 0.5 ml | 01/2010 | IM | | |
| H1N1 2009 Nasal | MedImmune | 0.1 ml | 01/2010 | Nasal | | SL |

Review of System:

Constitutional
Patient denied Fever in the last week.
EHT

| Chart | Administrative | Allergies | Encounters | Medication List | Problem List | Orders | Family Hx |
|---|---|---|---|---|---|---|---|

Neurological
Patient denied Headache associated with illness.

Vital Signs: 3230

Blood Pressure

| Artery | Body Side | | Position | | Pressure | | Flag |
|---|---|---|---|---|---|---|---|
| Brachial | Left | | Sitting | | 120/80 | | Normal |

Pulse

| Artery | Body Side | Rhythm | | Quality | | Pulse Rate | Flag |
|---|---|---|---|---|---|---|---|
| Radial | Left | Regular | | Normal | | 72 | Normal |

Respirations

| Rate | | Quality | | Rhythm | | Flag |
|---|---|---|---|---|---|---|
| 14/min | | Normal | | NORMAL | | |

Temperature

| Method | | Temperature F | Flag |
|---|---|---|---|
| Right Tympanic Membrane | | 101 | High |

Height, Weight and BMI

| Height | | Weight | | BMI | | Flag |
|---|---|---|---|---|---|---|
| 6'0" | | 220 (lb) | | 29.9 | | Overweight |

Physical Exam: 3240

EHT

Throat
Examination of the pharynx reveals the following: inflammation, exudate located diffusely this pathology is consistent with: bacterial infection.

Cardiovascular
Upon palpation of the chest wall there are no heaves, lifts, or thrills. The rate is normal, the rhythm is regular, S1 and S2 are normal, there are no murmurs, no gallops, and there are no rubs. There is no pitting edema of the lower extremities. There are no bruits. The peripheral artery pulses are 2+ brisk.

Respiratory
The patient is relaxed and breathes without effort. The patient is not cyanotic and does not use the accessory muscles of respiration. The AP diameter of the chest is normal. The chest expands symmetrically upon inspiration. Upon palpation of the chest wall there is no tenderness or masses. Tactile fremitus is normal and symmetrical. The lungs are clear to percussion. There are no crackles, wheezes, rhonchi, stridor or pleural rubs. There is no bronchophony, egophony, or whispered pectoriloquy.

| Chart | Administrative | Allergies | Encounters | Medication List | Problem List | Orders | Family Hx |

Gastrointestinal
The abdomen is soft and nontender, there is no guarding or rigidity. Bowel sounds are normal. There are no palpable masses. There is no hepatosplenomegaly. There is no costovertebral angle (CVA) tenderness

Musculoskeletal
  Spine Ribs
  Cervical Spine
  Osteopathic
  There is a somatic dysfunction on the right side. T- Tissue Changes; Tone 2 - Moderate increase in tone right. T- Tissue Changes; Texture 2 - Moderate increase in texture right.

Lymphatics
  Cervical
  The posterior auricular lymph nodes are palpable bilaterally they are: tender.  — 3245

Assessment: — 3250

| Diagnosis | Code | Problem | Comment |
|---|---|---|---|
| Acute Pharyngitis | 462 | Acute | |
| Nonallopathic Lesions Cervical Nec | 7391 | Acute | |

Coding: — 3255

| CPT IV Name | | Code |
|---|---|---|
| Strep A Assay W/optic | | 87880 |
| Osteopathic Manipulation | | 98925 |
| Office/outpatient Visit, Est | | 99213 |

Prescribe: — 3260

| Date | Medication | Sig | # | Refill | Status |
|---|---|---|---|---|---|
| 05/11/2010 | Amoxil 250 mg Cap | 1 TID | 30 | 0 | Active |

Orders:

| Order Date | Order No | Title | Ordering Provider | Result Status | Result In | Order Status |
|---|---|---|---|---|---|---|

| Chart | Administrative | Allergies | Encounters | Medication List | Problem List | Orders | Family Hx |
|---|---|---|---|---|---|---|---|

Osteopathic Manipulation
Office/outpatient Visit, Est

Prescribe: 3260

| Date | Medication | | | Sig | | Refill | Status |
|---|---|---|---|---|---|---|---|
| 05/11/2010 | Amoxil 250 mg Cap | | | 1 TID | | 30 0 | Active |

Orders:

| Order Date | Order No. | Title | | Ordering Provider | Result Status | Result In | Order Status |
|---|---|---|---|---|---|---|---|
| 05/10/2010 04:21 PM | 21061 | 87880 Strep A Assay W/optic | | Lizerbram S | Reviewed | 05/10/2010 04:22 PM | Accepted |

Osteopathic: 3270

Plan
High Velocity/Low Amplitude treatment techniques were used to treat the cervical spine. After treatment the somatic dysfunction was improved.

Follow Up: 3275

| Type | Recall Date | Provider Name | Notes |
|---|---|---|---|
| Follow-Up | 05/18/2010 | LIZERBRAM, SOL | |

Care Plan: 3280

Pharyngitis (bacterial)
Description: Description: This patient had a positive strep test. The patient will for strep pharyngitis. Antibiotics for 10 days. Advil for fever.

Problem List: 3285

| Description | Diagnosis | Onset Date | Resolution | Provider | Type | Status |
|---|---|---|---|---|---|---|
| Acute Pharyngitis | 462 | 05/11/2010 | | 378734 | Acute | Active |
| Nonallopathic Lesions Cervical Nec | 7391 | 05/11/2010 | | 378734 | Acute | Active |
| Mixed Hyperlipidemia | 2722 | 05/10/2010 | | 378734 | Chronic | Active |

ELECTRONIC MEDICAL SYSTEM TOUCH PHRASE TECHNOLOGY

BACKGROUND

The present disclosure relates generally to the field of computer software, applications and systems for medical examining, charting, and record keeping.

In general, the medical profession utilizes computer systems to maintain medical records, such as in an electronic medical record, for later retrieval and comparison. Such systems are typically historical in nature and require substantial human manipulation to enter medical data for use in making diagnosis based on trends, changes, and long term indicators as well as possibly for billing purposes.

Electronic systems utilized by medical practitioners at the point of care range from networked laptop computers to thin client workstations. These systems involve user interfaces consisting of text entry boxes and drop down menus. Generally, the nature of the user interfaces requires text entry by means of a computer keyboard.

Osteopathic practitioners may utilize electronic medical systems to record information from patient visits but, like non-osteopathic systems, such systems are not easy to use and often interfere in the patient experience.

SUMMARY

A representative embodiment relates to electronic medical system touch phrase technology including a method comprising initializing a touch phrase button by a processor such that the initializing associates a first text with the touch phrase button; receiving an input associated with the touch phrase button; updating a state of the touch phrase button based upon the input including associating a second text with the touch phrase button; and communicating the state of the touch phrase button to a memory device.

Another representative embodiment relates to a medical examination, charting and recording computer user interface that includes a method comprising displaying a first plurality of buttons at a user interface where the first plurality of buttons is associated with a first level of a data hierarchy; displaying a second plurality of buttons and a first plurality of touch phrase buttons in response to an input associated with the first plurality of buttons where the second plurality of buttons and the first plurality of touch phrase buttons are associated with a second level of the data hierarchy; receiving an input associated with a selected touch phrase button of the first plurality of touch phrase buttons; updating a state of the selected touch phrase button based upon the input; and communicating the state of the selected touch phrase button to a memory device where the state of the selected touch phrase button is associated with charting text configured for compilation in a report.

Yet another representative embodiment relates to an osteopathic examination, charting and record-keeping computer system includes a method comprising receiving subjective data associated with a patient examination where the subject data is configured for compilation in a medical chart; displaying a first plurality of buttons and a first plurality of touch phrase buttons, at a user interface; receiving an objective input associated with a selected touch phrase button of the first plurality of touch phrase buttons; updating a state of the touch phrase button in response to the objective input; communicating the state of the touch phrase button to a memory device where the state of the selected touch phrase button is associated with charting text configured for compilation in the medical chart; receiving assessment data associated with the patient examination where the assessment data is configured for compilation in the medical chart; and receiving plan data associated with the patient examination where the plan data is configured for compilation in the medical chart.

BRIEF DESCRIPTION OF THE DRAWINGS

FIG. 9 is a representative screen display of a chief complaint screen that is a start of a subjective portion of a SOAP examination.

FIG. 10 is a representative screen display of an interview question.

FIG. 11 is a representative screen display of an interview report.

FIG. 12 is a representative screen display for collecting a patient's medical history.

FIG. 13 is a representative screen display for collecting a patient's vital signs.

FIG. 16 is a representative screen display of an interface for entering data associated with a musculoskeletal system of a patient.

FIG. 17 is a representative screen display of an interface for entering data associated with a third level of a data hierarchy.

FIG. 18 is a representative screen display of an interface for entering data associated with an osteopathic level of a data hierarchy.

FIG. 20 is a representative screen display after a medical professional has entered additional data associated with a touch phrase button.

Figure 21:
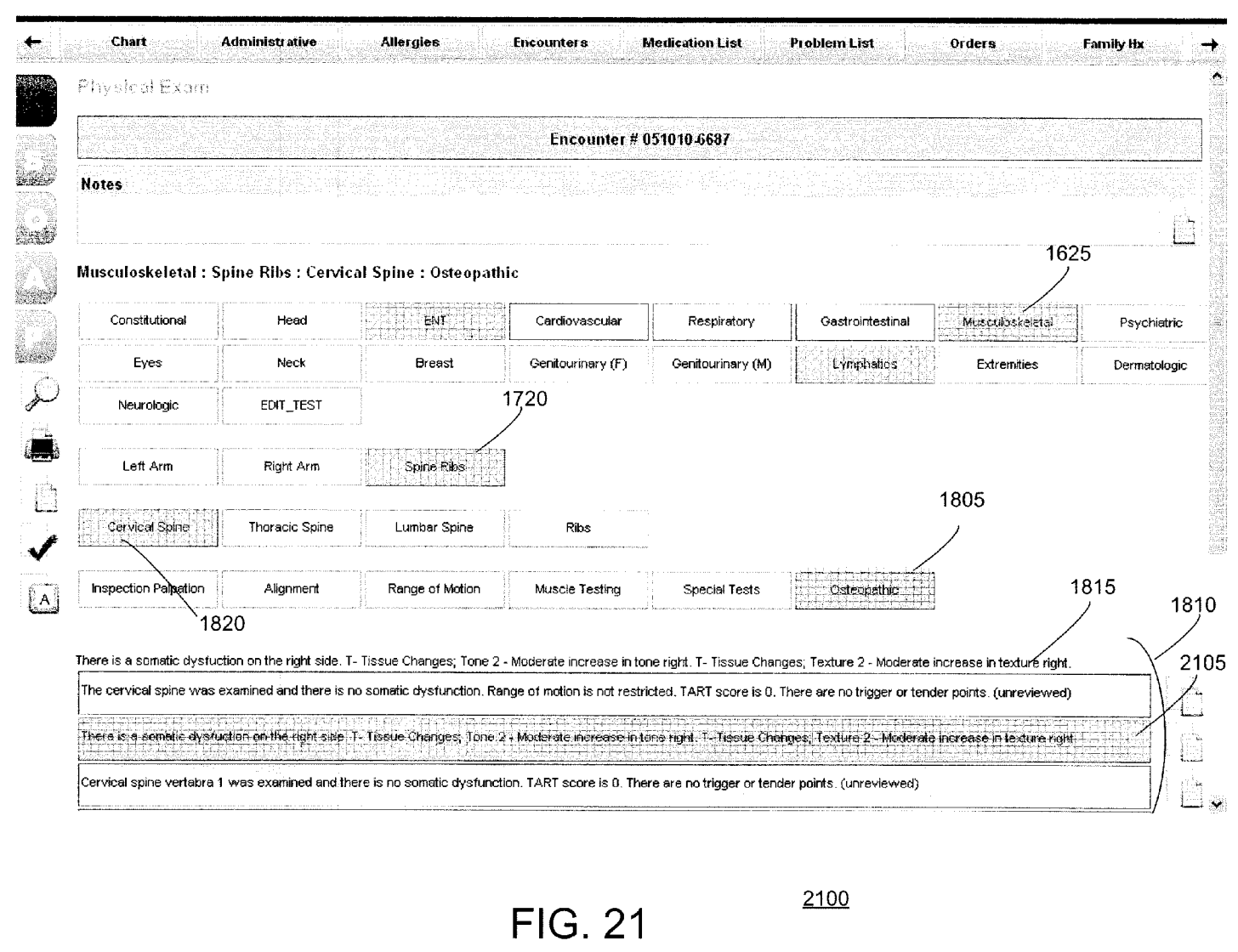

FIG. 21 is a representative screen display reflecting data entered during an examination.

FIG. 22 is a representative screen display of a physical examination summary.

FIG. 23 is a representative diagnosis screen display.

Figure 24:
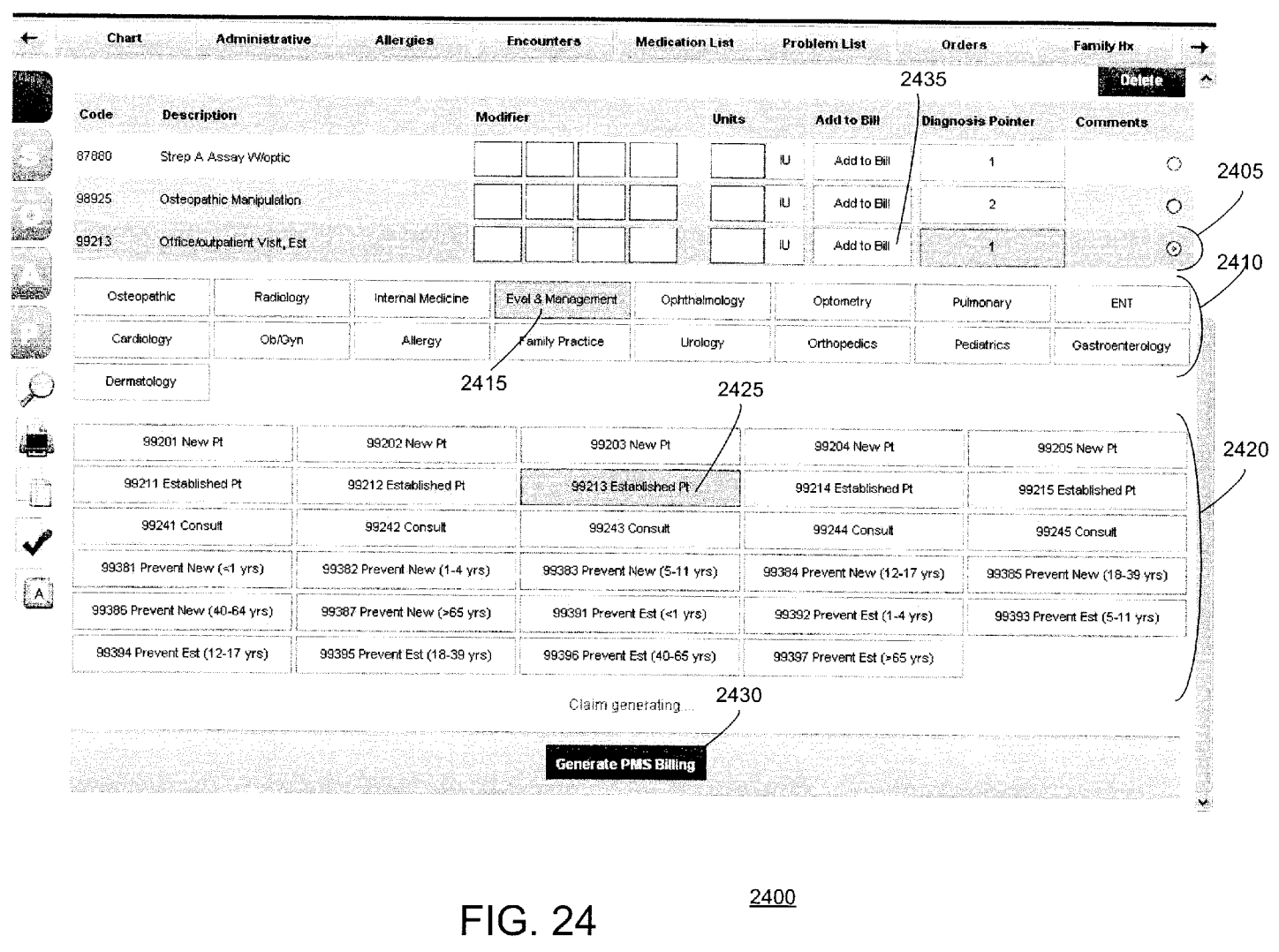

FIG. 24 is a representative procedure coding screen display.

FIG. 25 is a representative medication search screen display.

FIG. 26 is a representative screen display, displayed in response to an Amoxil 250 mg cap button being activated.

FIG. 31 is a representative osteopathic data entry screen display

FIG. 32A is a representative screen display of a portion of an examination summary.

FIG. 32B is a representative screen display of a portion of an examination summary.

FIG. 32C is a representative screen display of a portion of an examination summary.

FIG. 32D is a representative screen display of a portion of an examination summary.

FIG. 37 is a representative custom form creation screen display.

FIG. 38 is a representative screen display for selecting a first answer type.

FIG. 39 is a representative screen display for selecting a second answer type.

FIG. 40 is a representative custom form creation screen display.

DETAILED DESCRIPTION OF REPRESENTATIVE EMBODIMENTS

Representative embodiments are described below with reference to the accompanying figures. It should be understood that the following description is intended to describe representative embodiments and should not limit the claims.

Figure 1:
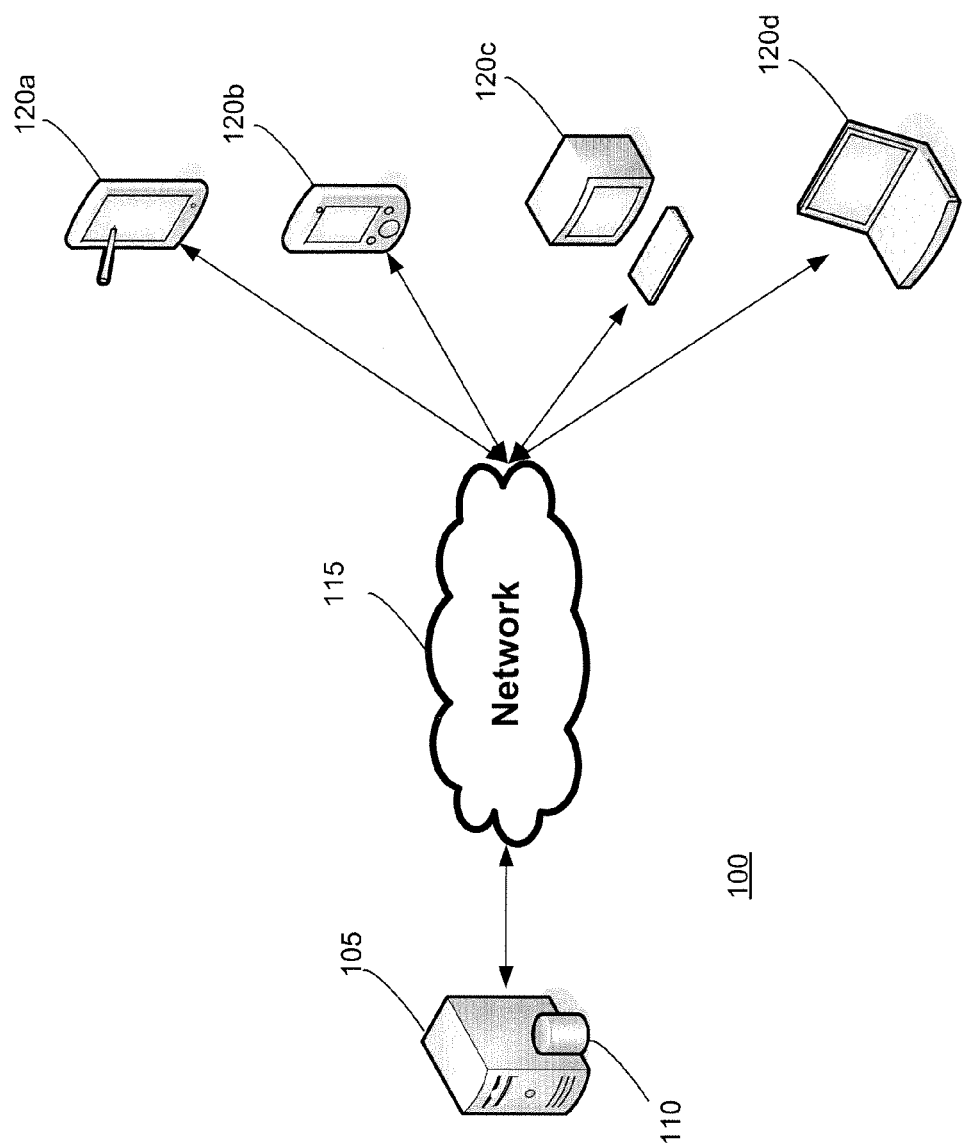
FIG. 1 is a representative overview of a healthcare management system.

FIG. 1 illustrates a representative overview for a healthcare management system 100. The healthcare management system 100 includes a computer 105 and a database 110. The database 110 may reside on the computer 105 or, in an alternative embodiment, reside on another computer or computers (not shown). In another embodiment, data may be located in multiple databases (not shown). The healthcare management system 100 may comprise, but is not limited to, a patient management application, a claims management application and an electronic health record application. The patient management application organizes management data relating to a practice. The management data may comprise, but is not limited to, patient data, appointment data, scheduling data, drug data, insurance data, and pharmacy data. Additionally, the patient management application, the claims management application, and the electronic health record application may be integrated with one another through a healthcare management framework. The healthcare management framework may be, but is not limited to, an application; a common data format; a common data storage; or an application programming interface.

The healthcare management system 100 is coupled to a network 115 by which the computer 105 can communicate with various devices 120a-d. Devices 120a-d can include a tablet computer 120a, a personal data assistant (PDA) 120b, a desktop computer 120c, and a notebook computer 120d. Devices 120a-d can also include, but are not limited to cell phones, netbooks, and other mobile devices. In one embodiment, devices 120a-d include a tablet computer that uses touch screen technology to receive user input, and does not rely on keyboards, mice, or styluses for receiving user input.

The devices 120a-d receive management data over the network 115. The management data is retrieved from the database 110. The management data may be modified by updating, deleting, or adding management data through devices 120a-d. The updated data may then be transmitted over the network 115 to the computer 105. The computer 105 may then update the database 110 accordingly.

Figure 2:
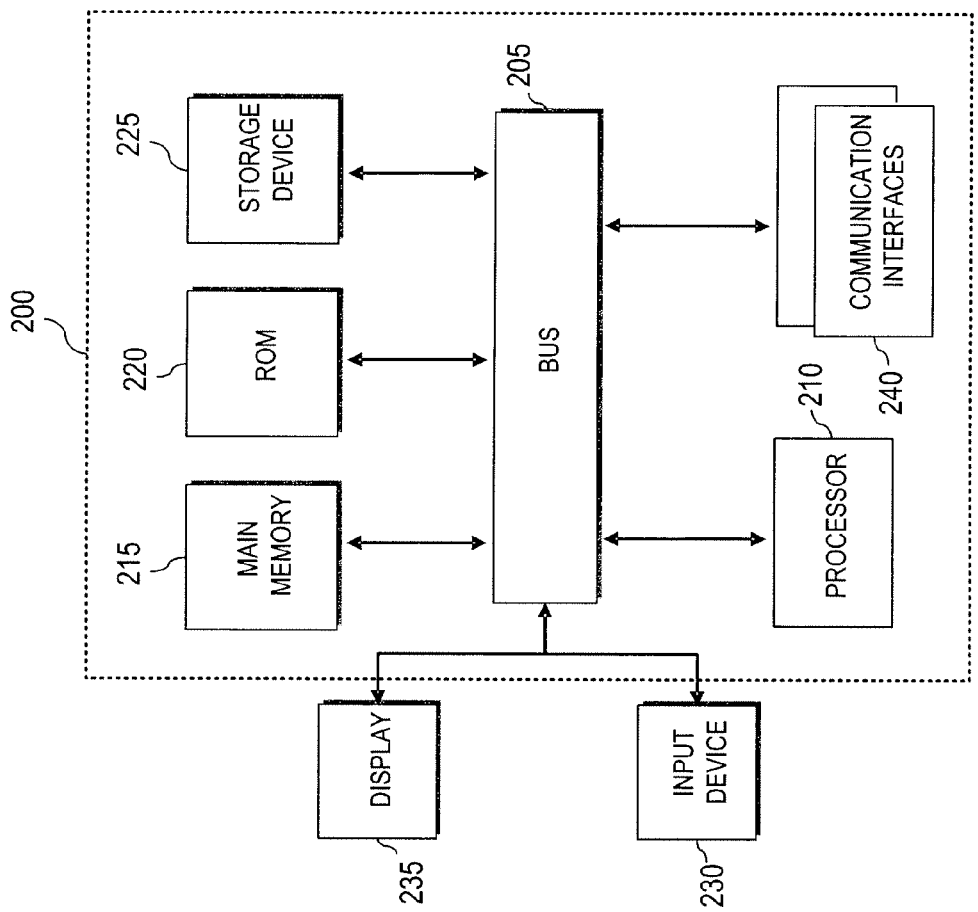
FIG. 2 is a depiction of a computer system in the healthcare management system of FIG. 1 upon which various embodiments can be implemented.

FIG. 2 illustrates a depiction of a computer system 200 representing representative hardware devices 120a-d upon which various embodiments can be implemented. The computing system 200 includes a bus 205 or other communication mechanism for communicating information and a processor 210 coupled to the bus 205 for processing information. The computing system 200 also includes main memory 215, such as a random access memory (RAM) or other dynamic storage device, coupled to the bus 205 for storing information and instructions to be executed by the processor 210. Main memory 215 can also be used for storing temporary variables or other intermediate information during execution of instructions by the processor 210. The computing system 200 may further include a read only memory (ROM) 220 or other static storage device coupled to the bus 205 for storing static information and instructions for the processor 210. A storage device 225, such as a solid state device, magnetic disk or optical disk, is coupled to the bus 205 for persistently storing information and instructions.

The computing system 200 may be coupled via the bus 205 to a display 235, such as a liquid crystal display, or active matrix display, for displaying information to a user. The display 235 may also be integrated into devices 120a-d. An input device 230, such as a keyboard including alphanumeric and other keys, may be coupled to the bus 205 for communicating information and command selections to the processor 210. In another embodiment, the input device 230 includes a touch screen display 235. The input device 230 can include a cursor control, such as a mouse, a trackball, or cursor direction keys, for communicating direction information and command selections to the processor 210 and for controlling cursor movement on the display 235.

According to various embodiments, the processes that effectuate representative embodiments that are forthcoming below can be provided by the computing system 200 in response to the processor 210 executing an arrangement of instructions contained in main memory 215. Such instructions can be read into main memory 215 from another computer-readable medium, such as the storage device 225. Execution of the arrangement of instructions contained in main memory 215 causes the processor 210 to perform the process steps described herein. One or more processors in a multi-processing arrangement may also be employed to execute the instructions contained in main memory 215. In alternative embodiments, hard-wired circuitry may be used in place of or in combination with software instructions to implement representative embodiments. Thus, embodiments are not limited to any specific combination of hardware circuitry and software.

The computing system 200 also includes at least one communication interface 240 coupled to bus 205. The communication interface 240 provides a two-way data communication coupling to a network link (not shown). The communication interface 240 sends and receives electrical, electromagnetic, or optical signals that carry digital data streams representing various types of information. Further, the communication interface 240 can include peripheral interface devices, such as a Universal Serial Bus (USB) interface, a PCMCIA (Personal Computer Memory Card International Association) interface, etc.

The at least one communication interface 240 may receive code transmitted from a remote device (not shown). The processor 210 may execute the transmitted code while being received and/or store the code in the storage device 225, or other non-volatile storage for later execution. In this manner, the computing system 200 may obtain application code in the form of a carrier wave.

Figure 3:
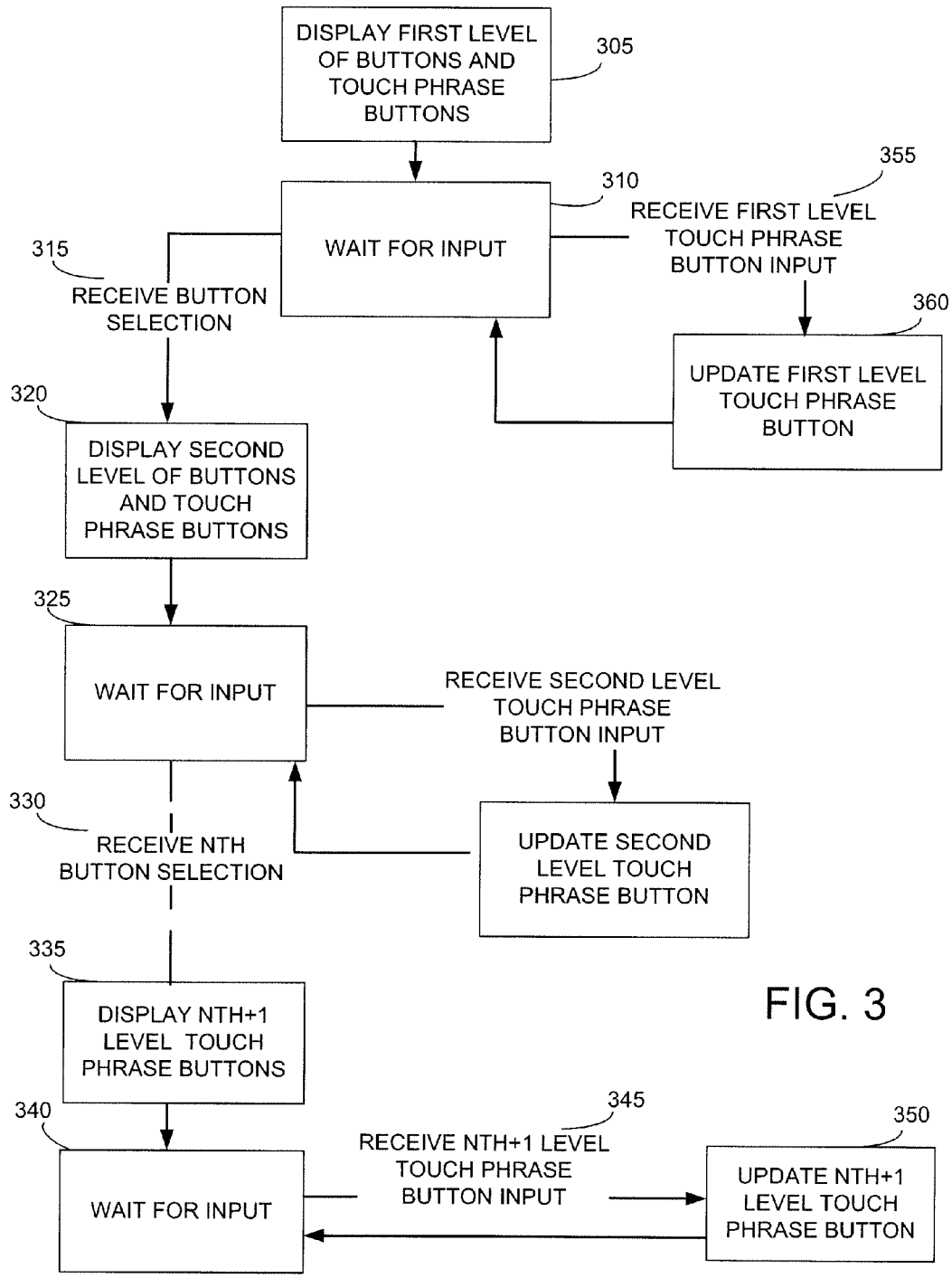
FIG. 3 is a flow diagram depicting representative operations performed for displaying a user interface for navigating a data hierarchy.

FIG. 3 is a flow diagram depicting representative operations performed for displaying a user interface for navigating a data hierarchy. Additional, fewer, or different operations may be performed depending on the particular embodiment. The user interface could be embodied on the computing system 200 described with reference to FIG. 2. Further, the user interface could be embodied in the patient management application, the claims management application, and the electronic health record application as part of the healthcare management system 100 described with reference to FIG. 1. The data hierarchy can consist of various levels of data. In addition, any level of the data hierarchy may include any number of nodes. A node can be one of a root node, internal node or a leaf node. An internal node has one or more child nodes. A node with no child nodes is a leaf node. In an operation 305, a first level of touch phrase buttons and a first level of buttons associated with a root node of the data hierarchy are displayed. Touch phrase buttons are more fully described below. In an operation 310, after the touch buttons and the buttons are displayed, the user interface waits for input.

An input associated with a first level touch phrase button may be received in an operation 355. In an operation 360, the state of the touch phrase button is updated. The updating of a state of a touch phrase button is described more fully below. After the touch phrase button's state is updated, the user interface returns to waiting for user input in the operation 310.

Alternatively, an input associated with a button from the first level of buttons is received in an operation 315. In response, a second level of buttons and a second level of touch phrase buttons are displayed in an operation 320. The first level of touch phrase buttons may be hidden based upon the receipt of the input in the operation 315. After displaying the second level of buttons and touch phrase buttons, the user interface waits for user input in an operation 325.

It should be noted that receiving an input associated with a second level of buttons results in a display of a third level of buttons and a third level of touch phrase buttons. The ability for an input associated with a particular level of button can be repeated to traverse to any level of the data hierarchy. In an operation 330, an input associated with a button that is associated with the nth level of the data hierarchy is received. In response, an nth+1 level of touch phrase buttons is displayed in an operation 335. At this nth+1 level, there are no buttons associated with the nth+1 level, which indicates that the last node in a particular path in the data hierarchy has been reached. After the nth+1 level of touch phrase buttons has been displayed, the user interface waits for user input in an operation 340. If input is received that is associated with a touch phrase button in an operation 345, the state of the touch phrase button is updated in an operation 350.

In a representative embodiment, only a latest selected level of touch phrase buttons is displayed. Touch phrase buttons associated with a previous level of the data hierarchy are not displayed. In another representative embodiment, a subset of the touch phrase buttons associated with previous levels of the data hierarchy is displayed along with the latest selected level of touch phrase buttons. The subset may include all previous levels of touch phrase buttons between the current level and the root level of the data hierarchy.

Figure 4:
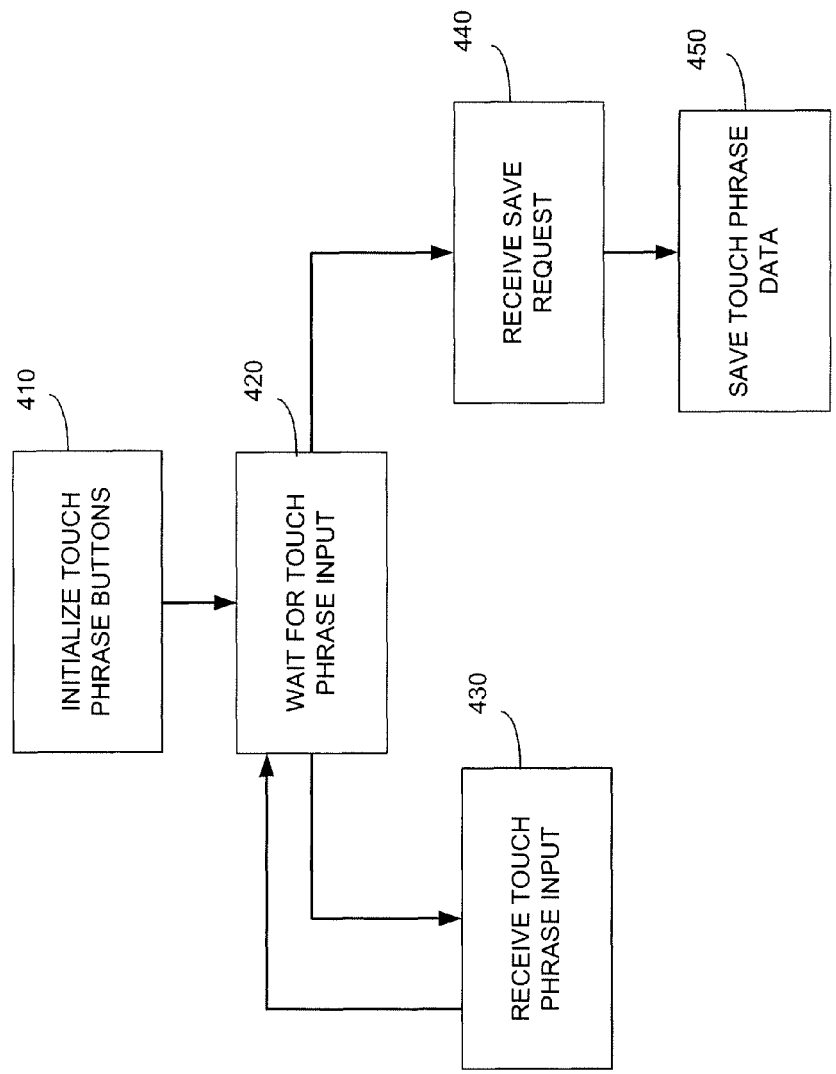
FIG. 4 is a flow diagram depicting operations that may be performed on a group of touch phrase buttons.

Each level of the data hierarchy is associated with a group of zero or more touch phrase buttons. Touch phrase buttons are distinct from typical user interface buttons in a number of ways as described below. FIG. 4 is a flow diagram depicting operations that may be performed on a group of touch phrase buttons. Additional, fewer, and different operations may be performed depending on the particular implementation. In an operation 410, the group of touch phrase buttons is initialized. Initialization includes determining a state for each touch phrase button. Initializing a touch phrase button may also include determining the touch phrase buttons' features. The features of a touch phrase button may include, but are not limited to, text, color, font, icon, data, and text formatting of the touch phrase button. Text of the touch phrase button can be a group of sentences, a sentence, a phrase, or a component of a phrase that can be included in a report. Because the text of touch phrase buttons is used in generating the report, the text is configurable. Configurable elements of touch phrase button can include, but are not limited to, the button's text, color, font, and text formatting. Further, the configurable elements can be associated with a particular state of the touch phrase button, thereby allowing the features of the touch phrase button to change based upon the state of the touch phrase button.

In an operation 420, the user interface waits for input. In an operation 430, the user interface receives input for a touch phrase button. As a result of the input, the touch phrase button's internal state changes. As part of the state change, the features of the touch phrase button are determined. Determination of the features may include retrieving the features locally or from a remote computer, such as the computer 105. After the operation 430, the user interface again waits for user input in the operation 420.

In an operation 440, a save request is received, and in an operation 450, the features associated with each touch phrase button may be saved. A touch phrase button's features are saved based upon the touch phrase button's state. Some potential states of a touch phrase button correspond to a no-save state. Touch phrase buttons that are in a no-save state when a save request is received do not have their features saved. Conversely, touch phrase buttons that are not in a no-save state, i.e., a save state, when a save request is received, do have their features saved. The touch phrase buttons' features may be saved locally, or may alternatively be saved to a remote database. For example, in one embodiment, the touch phrase buttons' features may be saved to the database 110 by transmitting the touch phrase buttons' features over the network 115. After the operation 450, the user interface may transition to a new display or may return to the operation 420. In an alternative implementation, the touch phrase data is saved after receiving the touch phrase input in the operation 430 without requiring a save request to be received.

Figure 5:
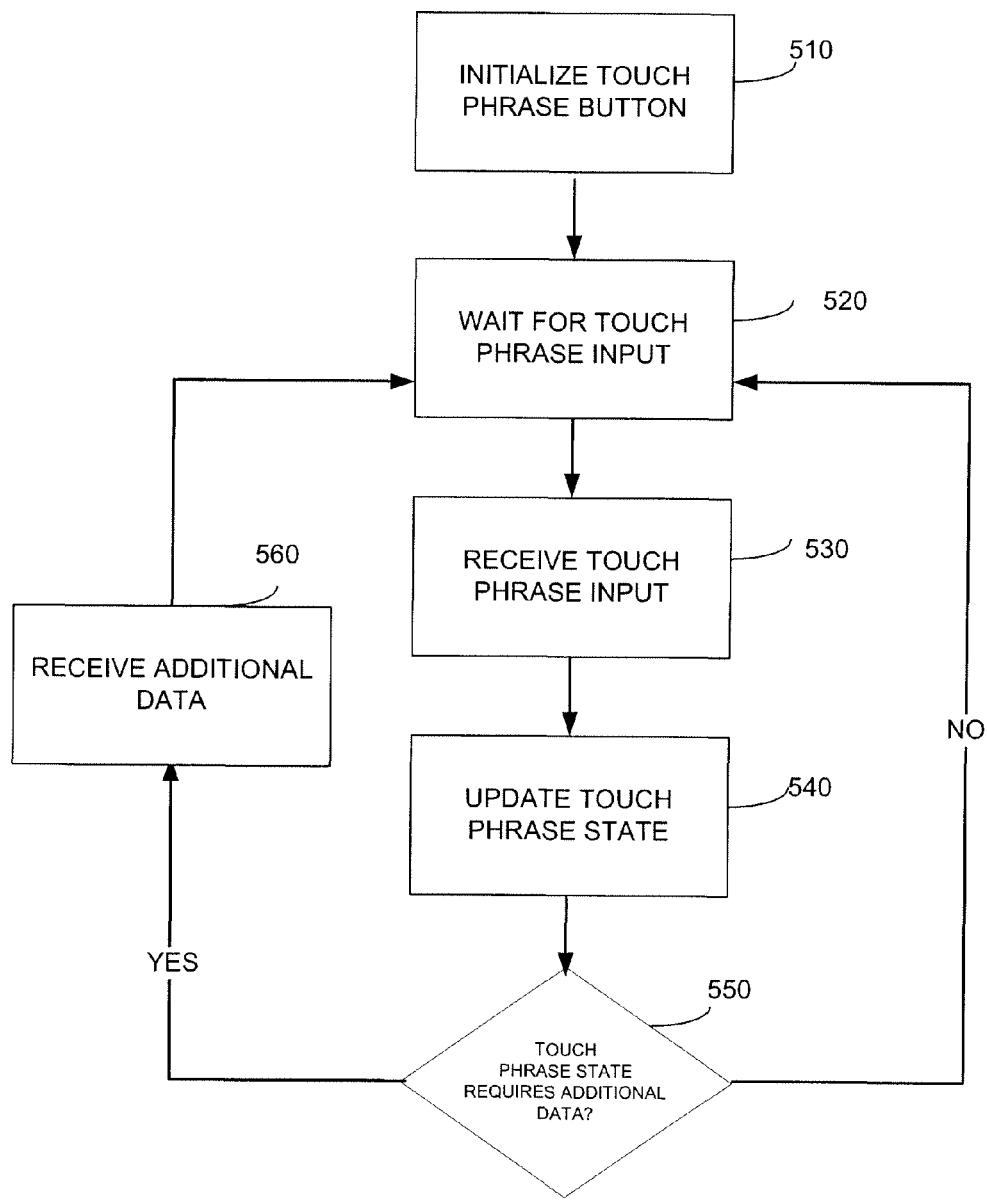
FIG. 5 is a flow diagram depicting operations of a single touch phrase button.

FIG. 5 is a flow diagram depicting operations of a single touch phrase button. Additional, fewer, and different operations may be performed depending on the particular implementation. The single touch phrase button may belong to a group of touch phrase buttons as described with reference to FIG. 4. In an operation 510, a touch phrase button is initialized. Initialization includes determining the feature's touch phrase button. In a representative embodiment, data associated with the touch phrase button's initialization may be retrieved from the computer 105 or the database 110. In an alternative embodiment, the features are retrieved from a local storage device. Once the touch phrase button is initialized, the user interface waits for input in an operation 520. In an operation 530, the user interface receives an input associated with the touch phrase button. In an operation 540, the state of the touch phrase button is updated to a new state based upon the input. In a representative embodiment, states of a touch phrase button are circular. For example, after initialization the touch phrase button is in a first state. As input is received for the touch phrase button, the state is transitioned to a new state. Continuing to receive input for the touch phrase button, the state of the touch phrase button eventually transitions to a last state. If input for the touch phrase button is received while the touch phrase button is in the last state, the touch phrase button transitions back to the first state. In one embodiment, if there is any additional data associated with a previous state of the touch phrase button, the additional data must be cancelled before transitioning to the next state. In an alternative embodiment, the additional data associated with the previous state of the touch phrase button remains associated with the previous state of the touch phrase button after the transition to the next state.

Updating the state of the touch phrase button may include updating various features associated with the touch phrase button. For instance, a color associated with the touch phrase button may change depending on the touch phrase button's state. As an example, the touch phrase button prior to receiving input may be blue in color. As a result of the input and the state change, the touch phrase button may change color to green. In addition, updating the state of the touch phrase button may include changing the button's internal state; changing the text, icon, font, or text formatting associated. In one embodiment, the features associated with a state change is retrieved from the database 110 or the computer 105. In another embodiment, the data associated with the state change is retrieved from the local storage.

Additional data associated with the touch phrase button may be received based upon the state of the touch phrase button. In an operation 550, it is determined if the touch phrase button requires additional data based upon the new state of the touch phrase button. If there is additional data associated with the new state, the data is retrieved in an operation 560. The additional data can be retrieved through the user input device 230, a touch screen, or from a remote data source. After the additional data is received, the user interface returns to waiting for input 520. If there is no additional data associated with the new state, the user interface returns to waiting for input 520.

Figure 6:
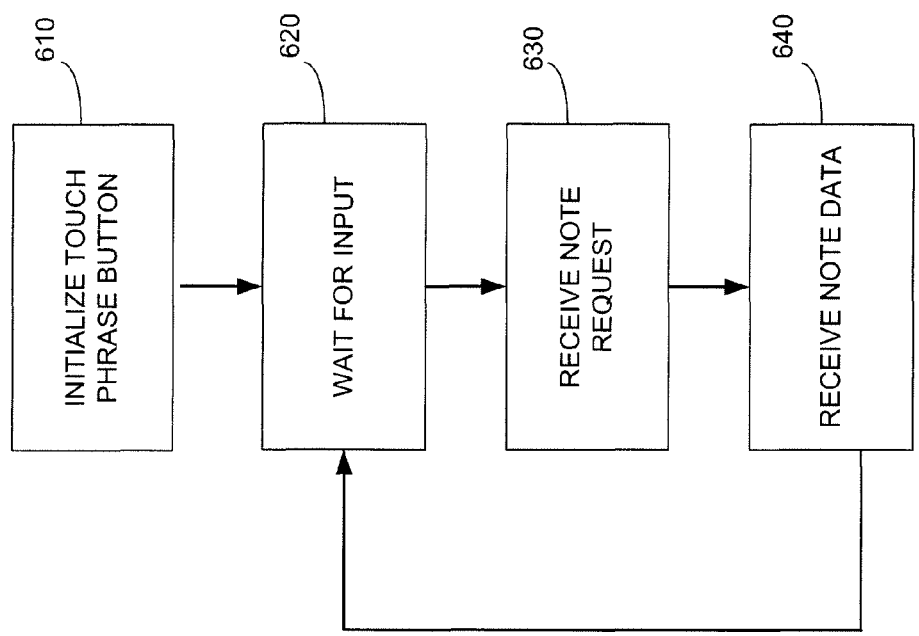
FIG. 6 is a flow diagram depicting operations performed for receiving a note data associated with a touch phrase button.

In addition to the configurable elements associated with a touch phrase button, each touch phrase button may also be associated with note data. FIG. 6 is a flow diagram depicting operations performed for receiving a note data associated with a touch phrase button. Additional, fewer, or different operations may be performed depending on the particular embodiment. In an operation 610, the touch phrase button is initialized as described above. After initialization a user interface waits for input in an operation 620. In an operation 630, the user interface receives a note request associated with the touch phrase button. The note data is received in operation 640. After the note data is received, the user interface returns to waiting for input in an operation 620. In one embodiment, the ability for a touch phrase button to receive note data is dependent upon the touch phrase button's state. For instance, in a default state a touch phrase button may not allow note data associated with the touch phrase button to be received. After a transition to a non-default state, the touch phrase button may allow note data to be received. In another embodiment, note data associated with the touch phrase button is allowed to be received regardless of the touch phrase button's state. In yet another embodiment, the touch phrase button may not allow note data to be received in any state.

Figure 7:
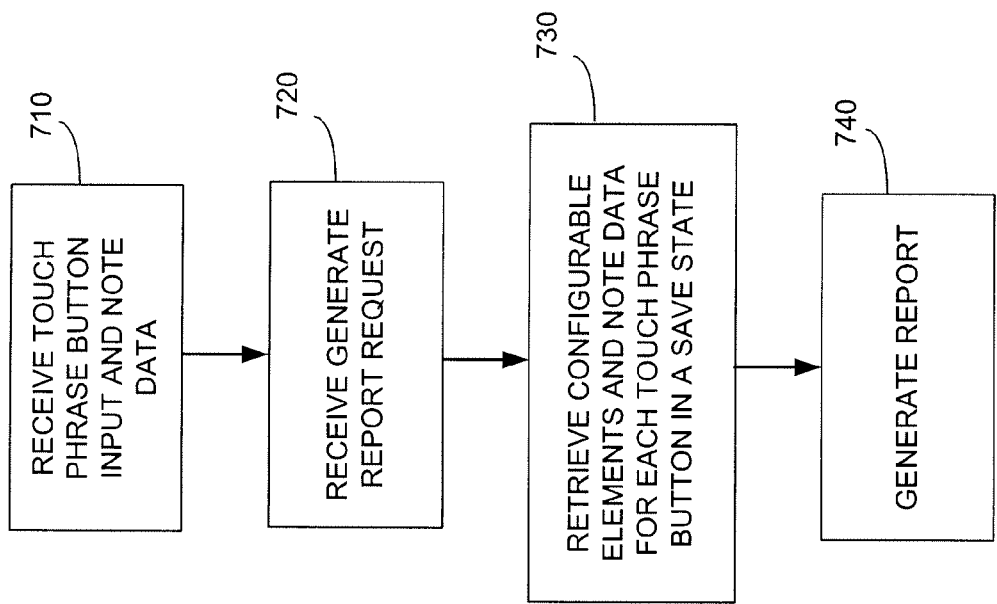
FIG. 7 is a flow diagram depicting operations performed in generating a report.

As noted above, touch phrase button input and data are used to generate a report. Specifically, the features and the note data associated with each touch phrase button are used to generate the report. FIG. 7 is a flow diagram depicting operations performed in generating the report. Additional, fewer, or different operations may be performed depending on the particular embodiment. In an operation 710, input and data for one or more touch phrase buttons is received as described with reference to FIGS. 4 through 6. In an operation 720, a generate report request is received. In an operation 730, each touch phrase button in an application is examined. Features and note data for each touch phrase button in a save state are retrieved. In one embodiment, the report includes text of all of the touch phrase buttons that were saved in a save state. Additionally, the note data associated with the touch phrase buttons are included in the report. In an alternative embodiment, the examination record includes the text of a subset of touch phrase buttons that were previously saved. For example, the report may contain only the text of touch phrase buttons in a particular level of the data hierarchy.

In an alternative embodiment, the report is updated as each touch phrase button is saved. In this alternative embodiment, the report is updated in a piecemeal fashion as touch phrase button input and data are saved. The generation step in this embodiment, therefore, causes the report to be displayed or printed, but does not generate the report.

FIGS. 8 through 32D illustrate representative screen displays of a representative electronic health record application. The electronic health record application may be integrated into the healthcare management system 100, as described with reference to FIG. 1, using the health management framework. The electronic health record application may be embodied on devices 120a-d, and in addition may send and receive data from the computer 105 or the database 110. The examination application provides a representative embodiment of navigating a data hierarchy as described with reference to FIG. 3. In addition, a representative embodiment of touch phrase buttons as described with reference to FIGS. 4 through 6 is illustrated. Finally, the electronic health record application provides a representative embodiment of generating a report as described with reference to FIG. 7.

Figure 8:
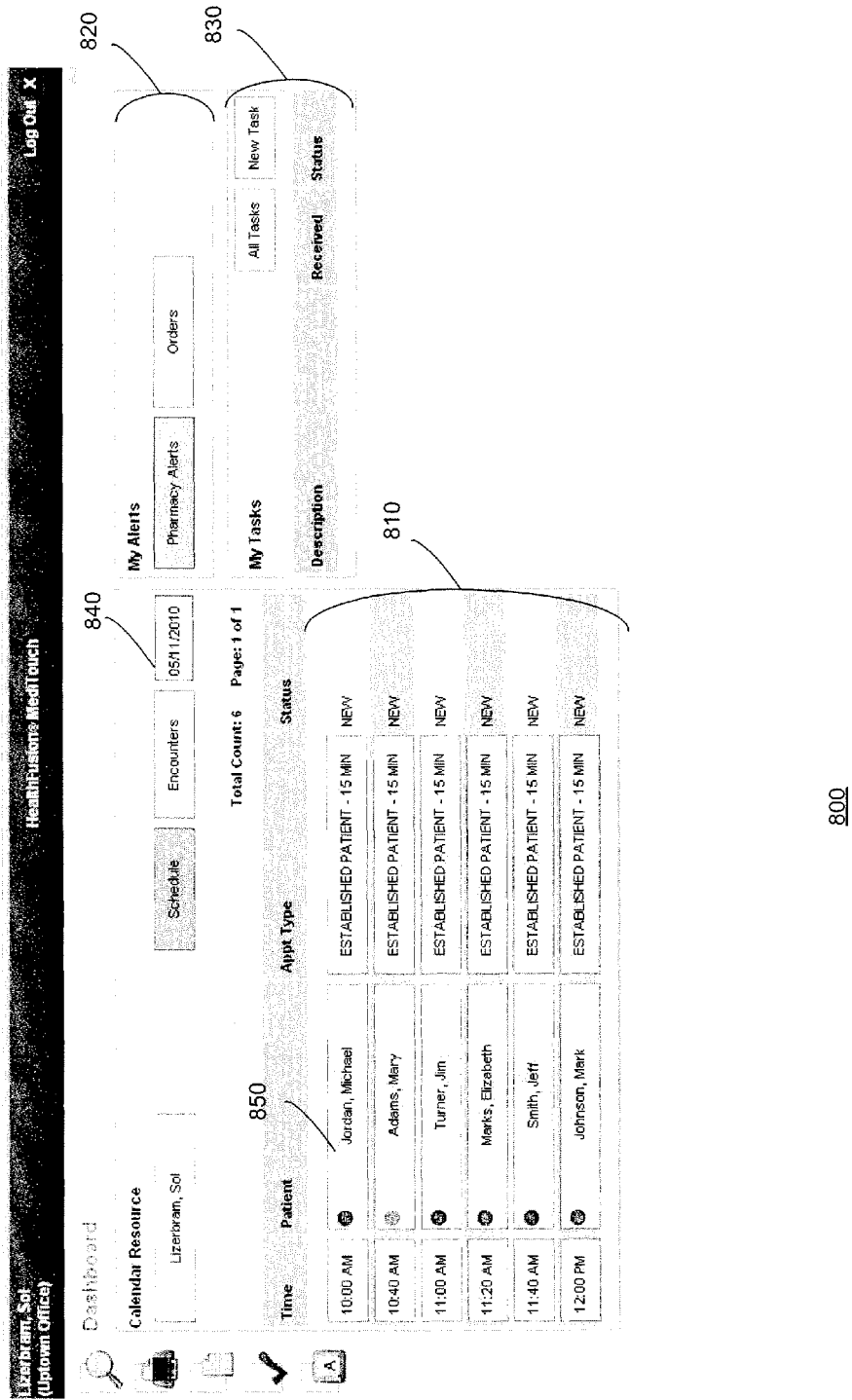
FIG. 8 is a representative screen display of a dashboard screen of an electronic health record application.

FIG. 8 is a representative screen display of a dashboard screen 800 of the electronic health record application. The dashboard screen 800 includes a listing of appointments 810; alerts 820; and tasks 830 for a medical professional. The listing of appointments 810 in this display 800 are for a particular day, Jun. 11, 2010, as expressed in a date selection box 840. Other dates as well as date ranges could be chosen using the data selection box 840. Portions of data displayed on the dashboard screen 800 may be retrieved from the patient management application via the healthcare management framework. Data corresponding to the appointments, tasks and alerts can be retrieved from a local storage device or from the computer 105 or the database 110.

A patient's information can be retrieved by activating a button 860 associated with the patient button. Buttons in the patient management application can be activated based upon the input device 230 as described with reference to FIG. 2. For example, a button may be activated based upon input received from a touch screen. After activating the button 850, the medical professional can review patient data relating to the patient. The patient data can include, but is not limited to, the patient's past medical history, social history, immunization history, allergies, prescribed medications and family history. Activating the button 850 also allows the medical professional to enter patient data associated with a patient examination. As a result of the entering of the patient data, the patient's electronic health record is updated accordingly. The representative electronic health record application is configured for the collection of the patient data based upon the patient examination conducted according to a subjective, objective, assessment, and plan (SOAP) convention.

Figure 9:
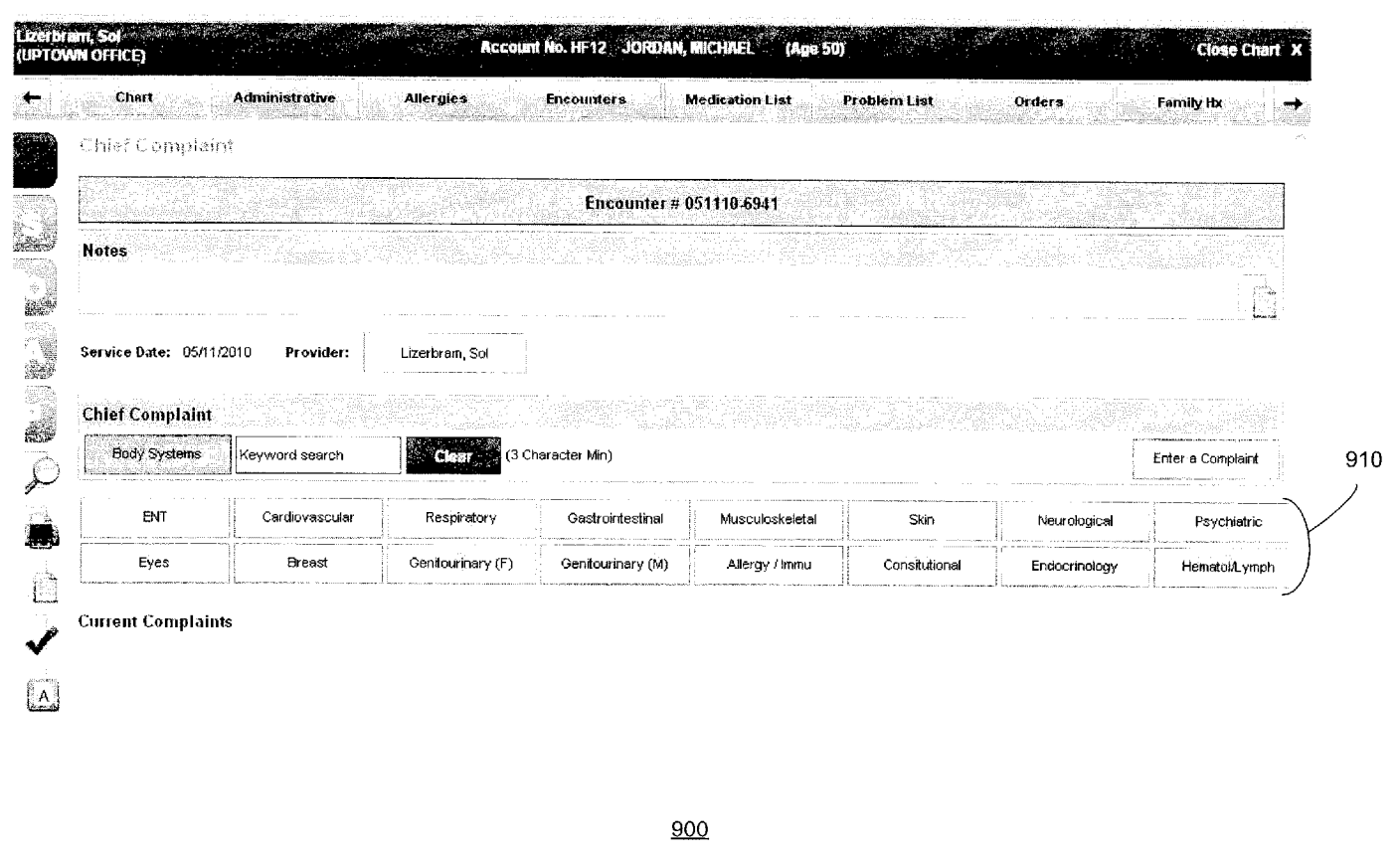
Figure 10:
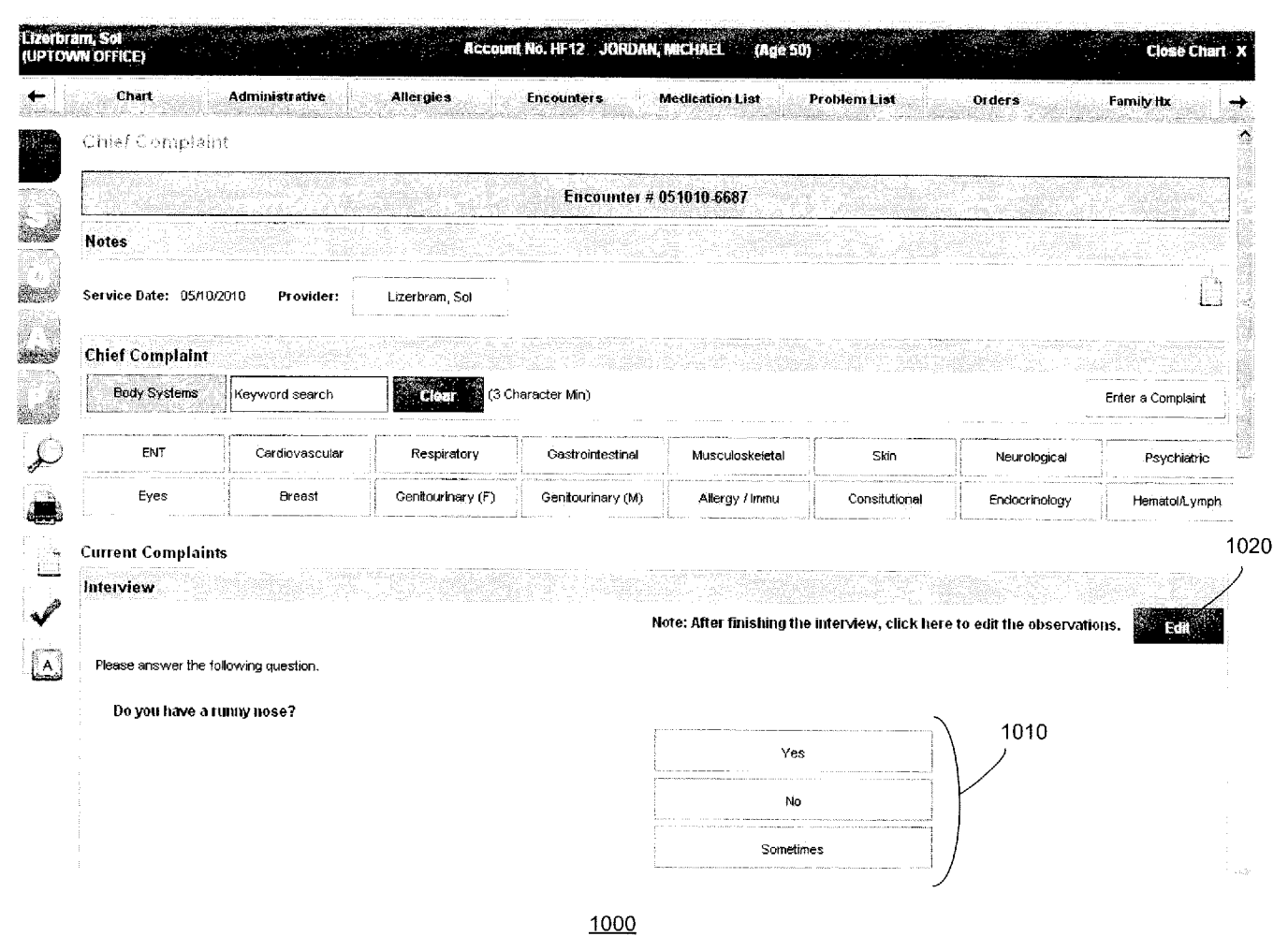
Figure 11:
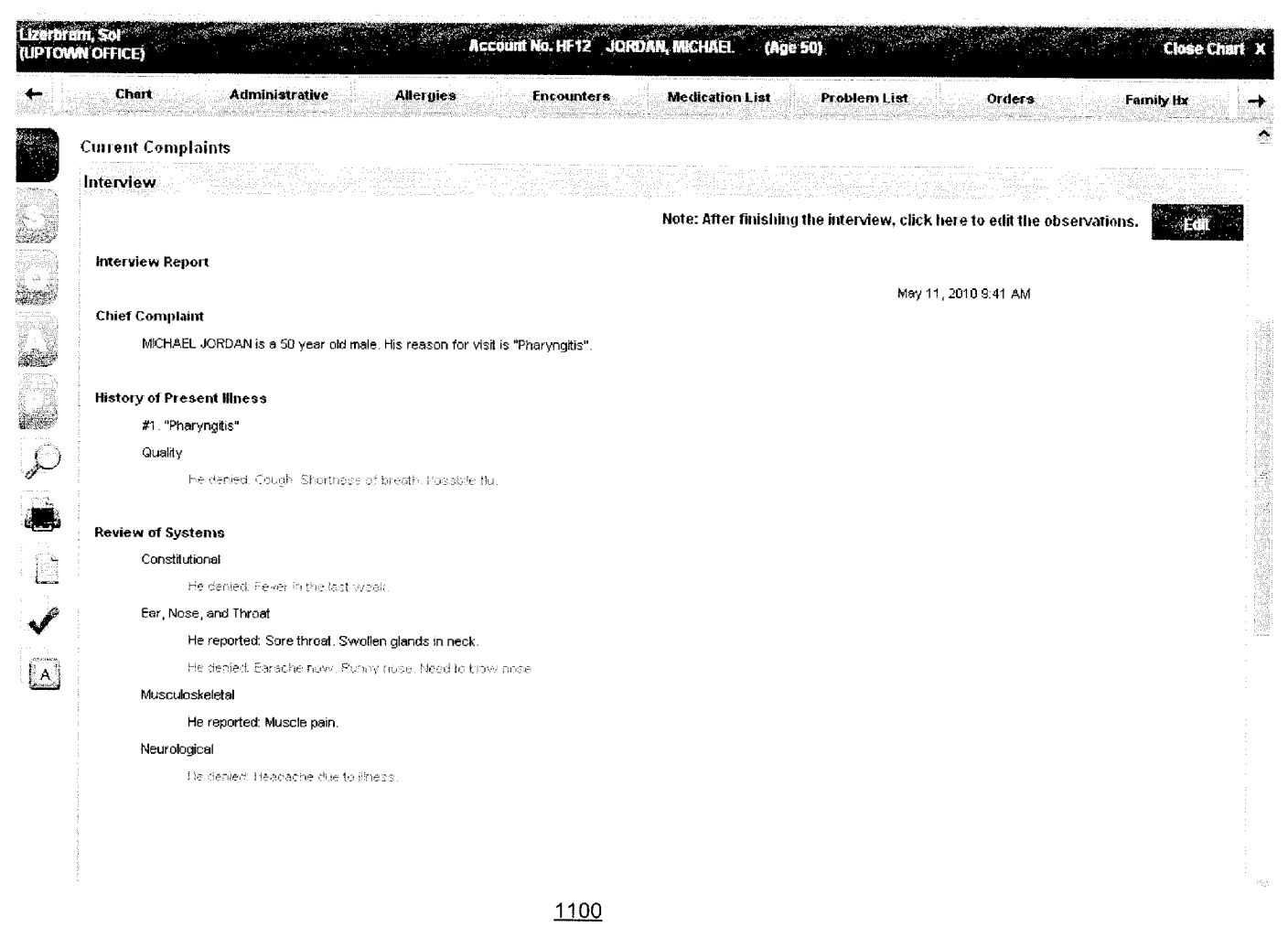

FIG. 9 is a representative screen display of a chief complaint screen 900 that is a start of a subjective portion of a SOAP examination. The chief complaint screen 900 allows the medical professional to record reasons for the patient's appointment. Complaints are chosen by activating various complaint buttons 910 based upon information provided by the patient. Following the selection of the patient's chief complaint, various screens are presented that facilitate a patient interview. FIG. 10 provides a representative screen display 1000 of an interview question. The patient interview consists of questions and associated answers. The questions and the associated answers are configurable based upon the patient data. For example, the questions asked during the patient interview regarding a skin complaint would be different than the questions asked during the patient interview regarding a complaint regarding the patient's eyes. In another example, questions could be configured only to be presented based upon, but not limited to, the patient's sex, medical history, family history, and answers to previous questions. Patient data is recorded based upon activation of one of a group of buttons 1010 that correspond to various responses. An edit button 1020 allows a medical professional to edit collected data associated with the patient interview. After the patient interview is completed an interview report is generated. FIG. 11 is a representative screen display 1100 of the interview report. The report is generated based upon the collected data from previous screens, such as the screen display 1000 of FIG. 10.

Figure 12:
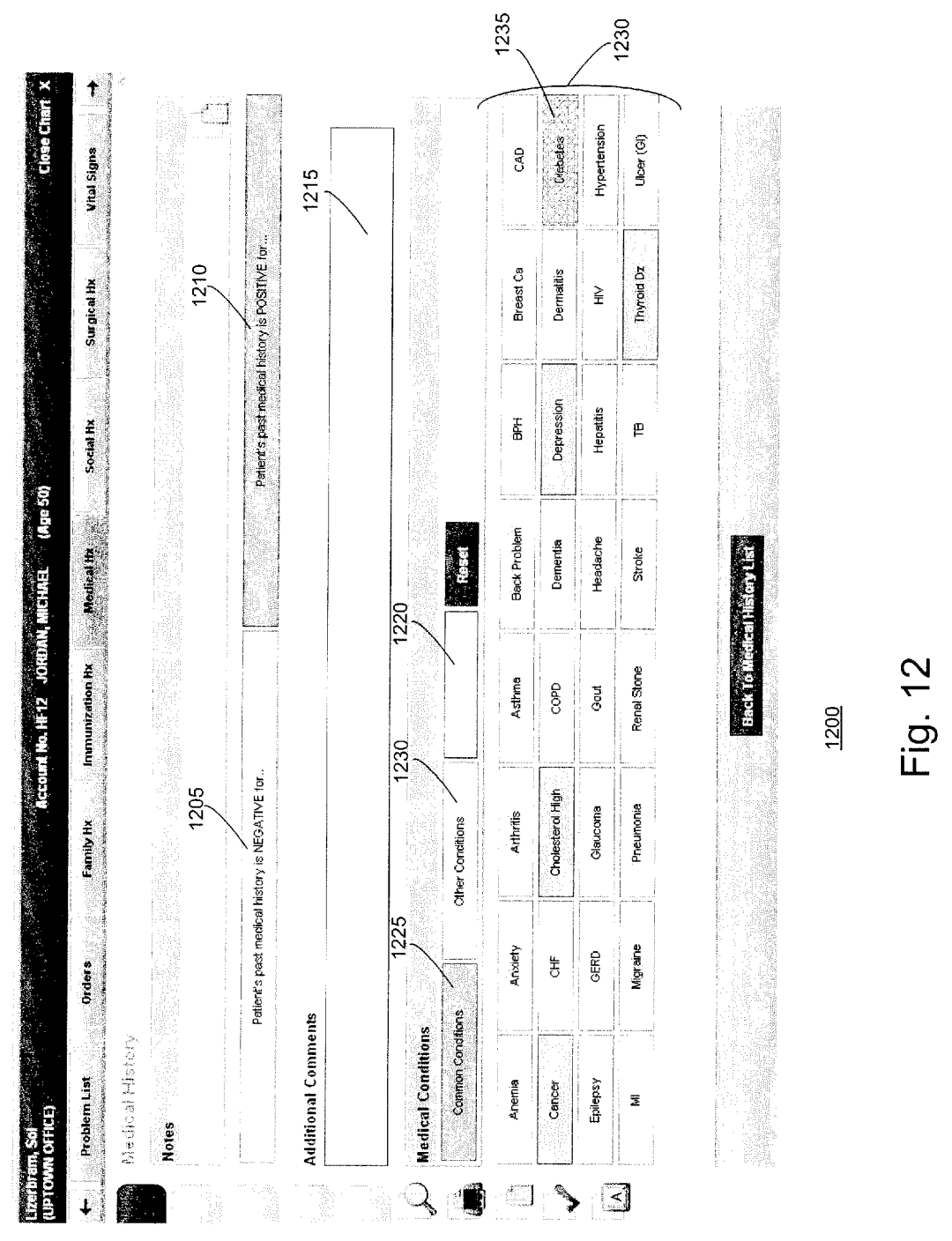

The patient examination may also provide an opportunity for the medical professional to collect data regarding the patient's history. The data regarding the patient's history may include, but is not limited to, the patient's immunization history, known allergies, surgical history, previous prescriptions, social history, family history, and medical history. A representative screen display 1200 for collecting the patient's medical history is illustrated in FIG. 12. To enter conditions that are not present in the patient's medical history, button 1205 is activated. The medical professional can then activate any of the conditions from the common conditions group of buttons 1230. The buttons that are in the common conditions group of buttons 1230 are displayed based upon the activation of the common conditions button 1225. This group of buttons may also be displayed when the patient's medical history screen display 1200 is first displayed, without requiring activation of button 1225. Condition buttons that are associated with the common conditions group of buttons are configurable. For example, the common conditions group of buttons 1225 may include a breast cancer condition button for a female patient. For a male patient, however, the common conditions group of buttons may replace the breast cancer condition button with a testicular cancer condition button, for example. In addition, the medical professional could add common condition buttons for all patients based upon the medical professional's practice. Medical professionals are not limited to selecting only those conditions from the common conditions group of buttons 1225. The medical professional may also search for other conditions using the search box 1220. The other conditions button 1230 also provides the medical professional with other condition buttons. When activated, the other conditions button 1230 displays another group of condition buttons (not shown) that the medical professional can choose from.

The medical professional can also select conditions that are present in the patient's medical history. This is done by activating the button 1210. Any condition that has been previously selected as not being present in the patient's medical history has its corresponding condition button deactivated. In a deactivated state, a condition button does not allow the medical professional to activate the condition button. This ensures that a condition is not selected as both present and not present in the patient's medical history. For example, a diabetes button 1235 was previously selected as not being present in the patient's medical history. When button 1210 is activated, the diabetes button 1235 is deactivated, as shown with hatching of the diabetes button 1235. The diabetes button 1235 would be reactivated if button 1205 is activated. After activating the button 1210, the medical professional can then select conditions in a similar way as described above. At any point during inputting the patient's medical history, the medical profession can enter any additional notes in a text area 1215.

FIG. 12 provides a representative screen display 1200 for collecting the patient's medical history. The electronic health record application may also contain screen displays for collecting the patient's data relating to the patient's immunization history, known allergies, surgical history, previous prescriptions, social history, and family history.

Figure 13:
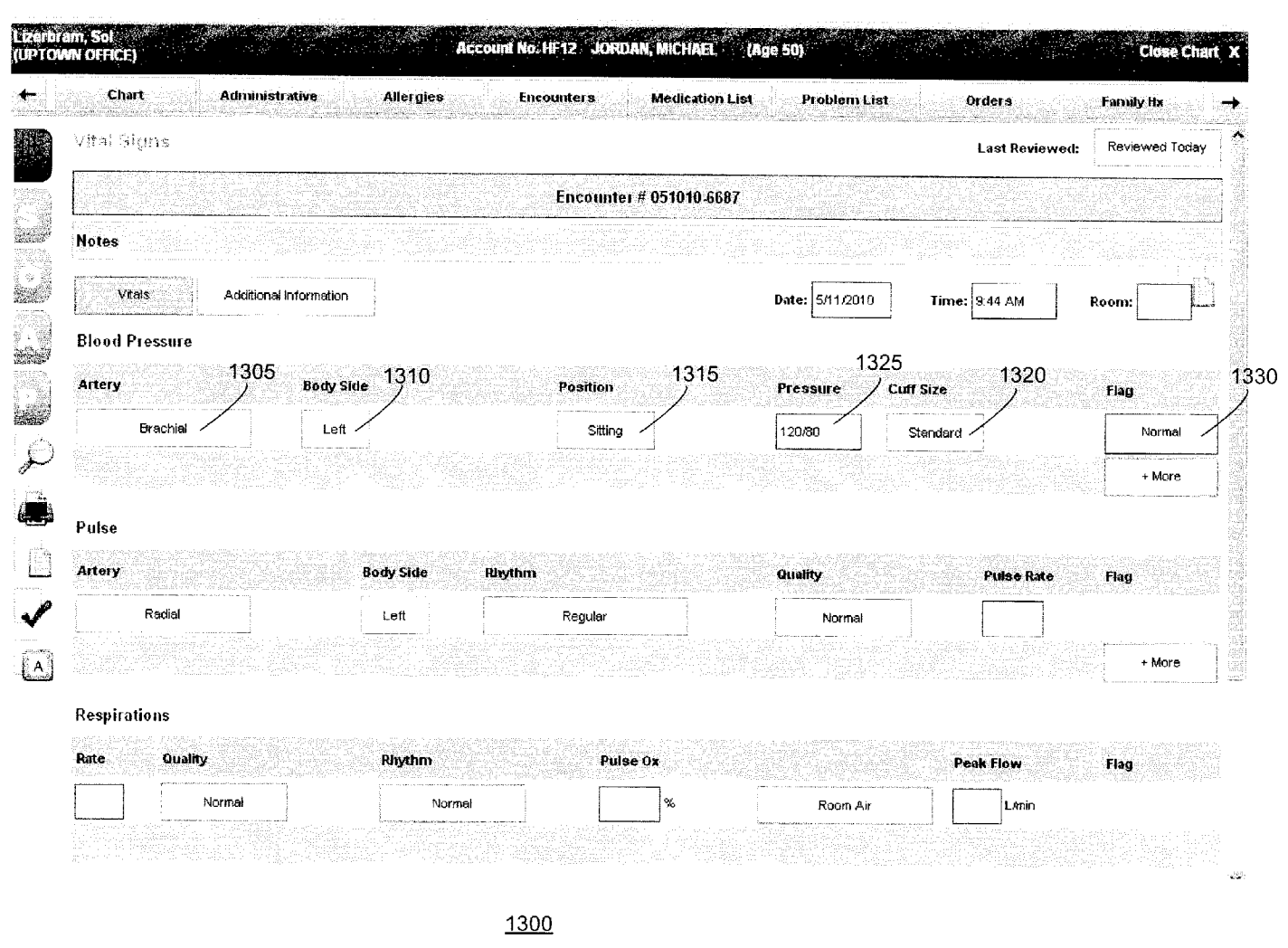

After the subjective portion of the patient examination is complete, the medical professional can start the objective portion of the patient examination. In the objective portion of the patient examination, various physical examination findings are detected and recorded. FIG. 13 provides a representative screen display 1300 for collecting the patient's vital signs. As an illustrative example of collecting vital sign data, the medical professional can record a patient's blood pressure. Using buttons 1305, 1310, 1315, and 1320, the medical professional selects the patient's artery, body side, position, and cuff size used to collect the patient's blood pressure. Activating one of the buttons 1305, 1310, 1315, and 1320 allows the medical professional to change text associated with the button. For example, activating the button 1310 allows the medical professional to choose the left or right side of the patient used to collect a blood pressure reading. Different options can be presented to the medical professional using a drop down list or a separate dialog window. Alternatively, activating the button 1310 may change the button to a next text value. For example, when current text for button 1310 is "Left," upon activation, the text corresponding to button 1310 changes to "Right." A blood pressure reading can be input in a user interface element 1325. The user interface element 1325 can be, but is not limited to, a text field, a separate dialog or a drop down list.

After entering the blood pressure reading, a flag 1330 is displayed. The flag 1330 allows additional information to be presented based upon a recorded vital sign. In this current example, the patient's blood pressure was entered as 120/80 in the user interface element 1325, which is in a normal range. The flag 1330, therefore, provides an indication that the data was in a normal range. The flag 1330 can provide this indication based upon the flag's text and color. In addition, the flag's various options are configurable. For example, flag 1330 could have indications including, but not limited to, a slight danger, a moderate danger, and a great danger indication that is based upon various blood pressure levels. Each vital sign has a corresponding flag, and that flag has a group of indications that correspond to various levels of the vital sign.

Figure 14:
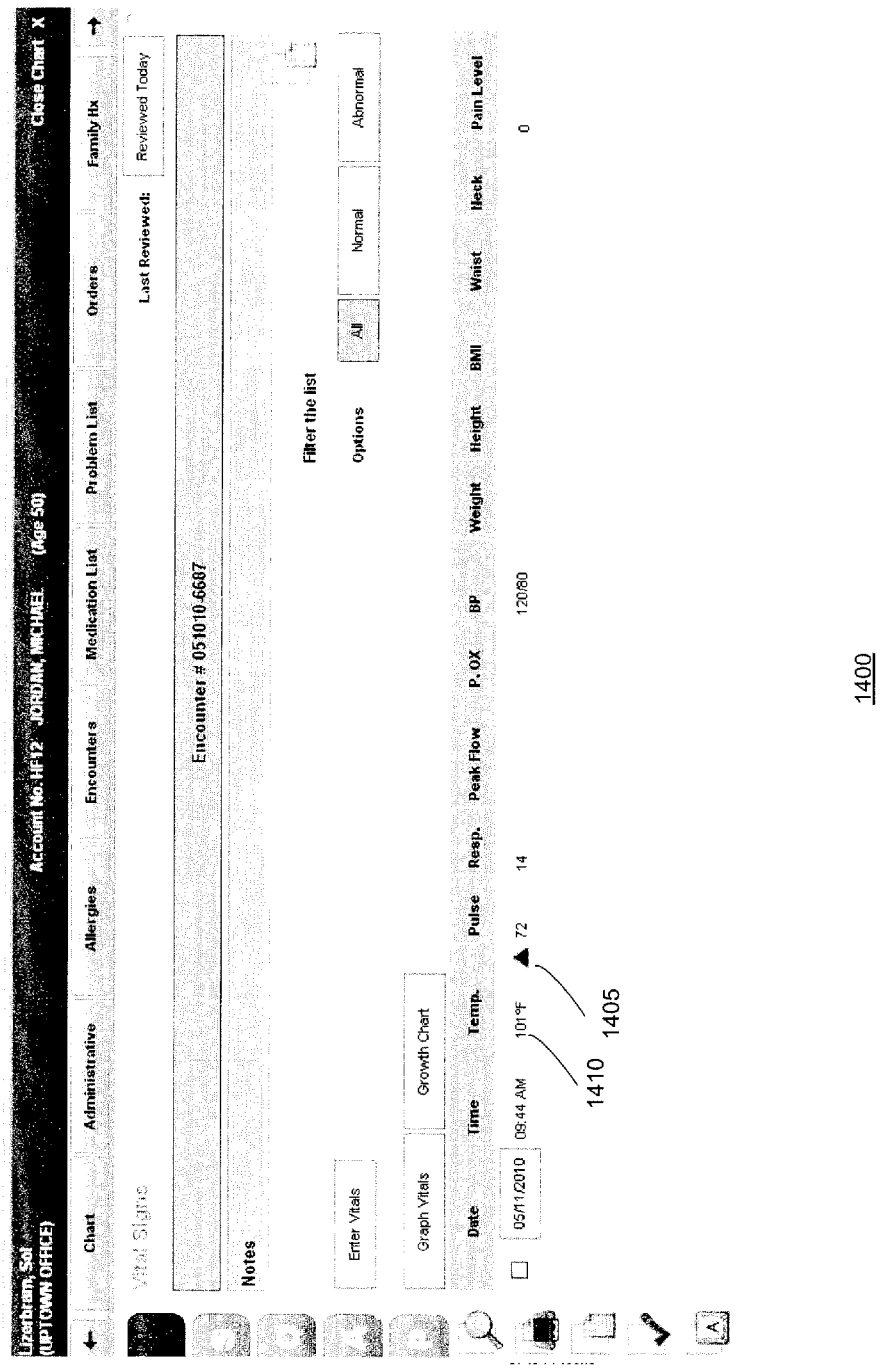
FIG. 14 is a representative vital sign overview screen display.

After entering all the requisite vital signs, a vital sign overview screen display 1400, as illustrated in FIG. 14, can be displayed. This screen display 1400 provides the medical professional with an overview of the patient's recorded vital signs. Vital signs recorded during a previous examination can also be displayed on this screen. An indication may appear next to each vital sign. For example, the indication 1405 is shown to the right of patient's temperature 1410. Each indication is configurable based upon a vital sign's value. An indication can also be configured not to be displayed based upon a vital sign's value.

After the requisite vital signs are collected, the electronic health record application allows the medical professional to enter patient data related to a physical examination portion of the patient examination. FIGS. 15 through 18 illustrate representative screen displays of an interface for entering the patient data associated with the physical examination. The interface is a representative embodiment of navigating a hierarchy of data as discussed with reference to FIG. 3.

Figure 15:
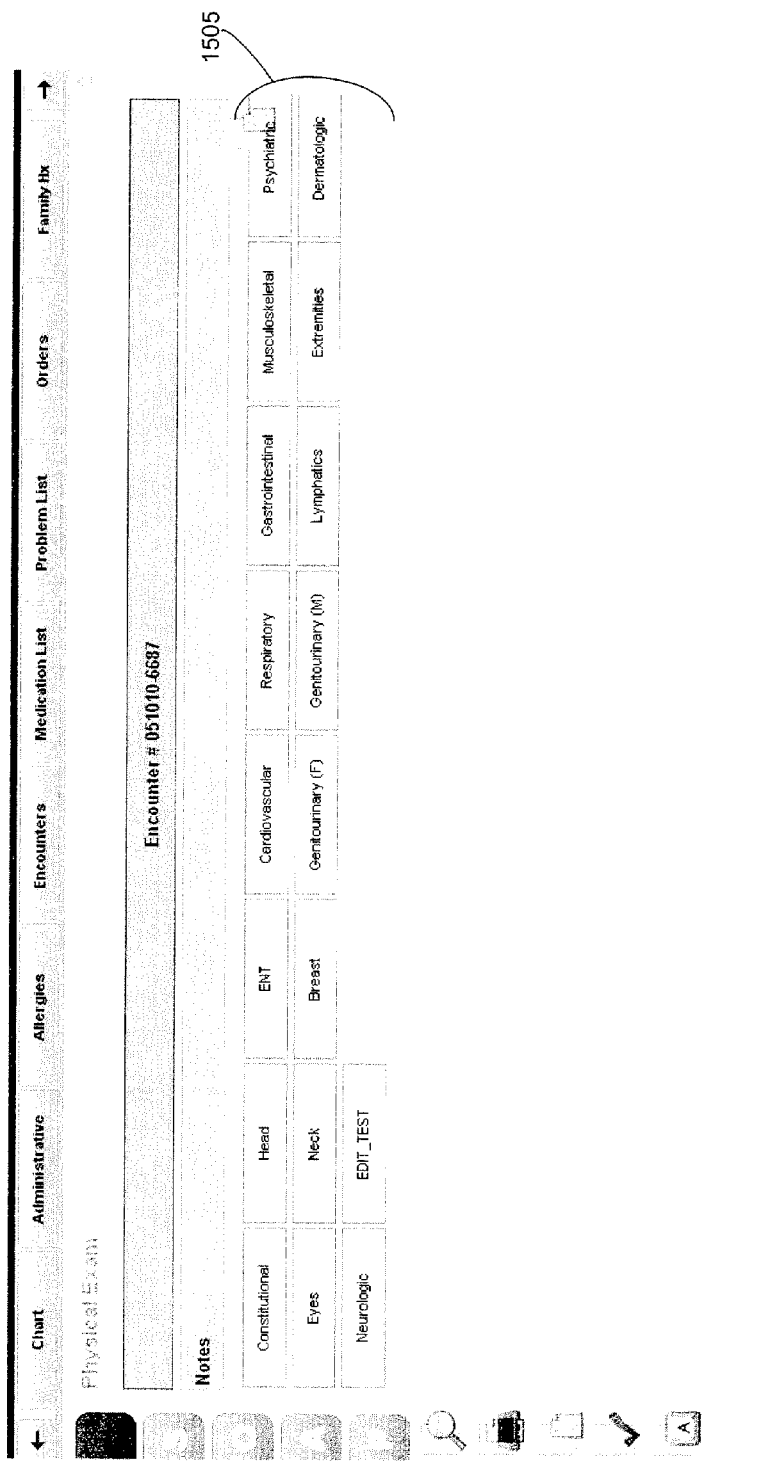
FIG. 15 is a representative screen display for collecting data relating to a physical examination.

FIG. 15 is a representative screen display 1500 for collecting data relating to the physical examination. The display 1500 includes a first level group of buttons 1505 that corresponds to a first level of a data hierarchy. In this representative screen display, the first level of the data hierarchy corresponds to various organ systems of the patient. The buttons that are in the first level group of buttons 1505 may change based upon previously entered data. For instance, a button may be displayed based upon the patient's previously recorded vital signs or medical history. The text associated with a button may also change based upon previously entered configuration data or patient data. In an alternative implementation, a first level group of touch phrase buttons (not shown) may also be presented that is associated with the first level of the data hierarchy.

Figure 16:
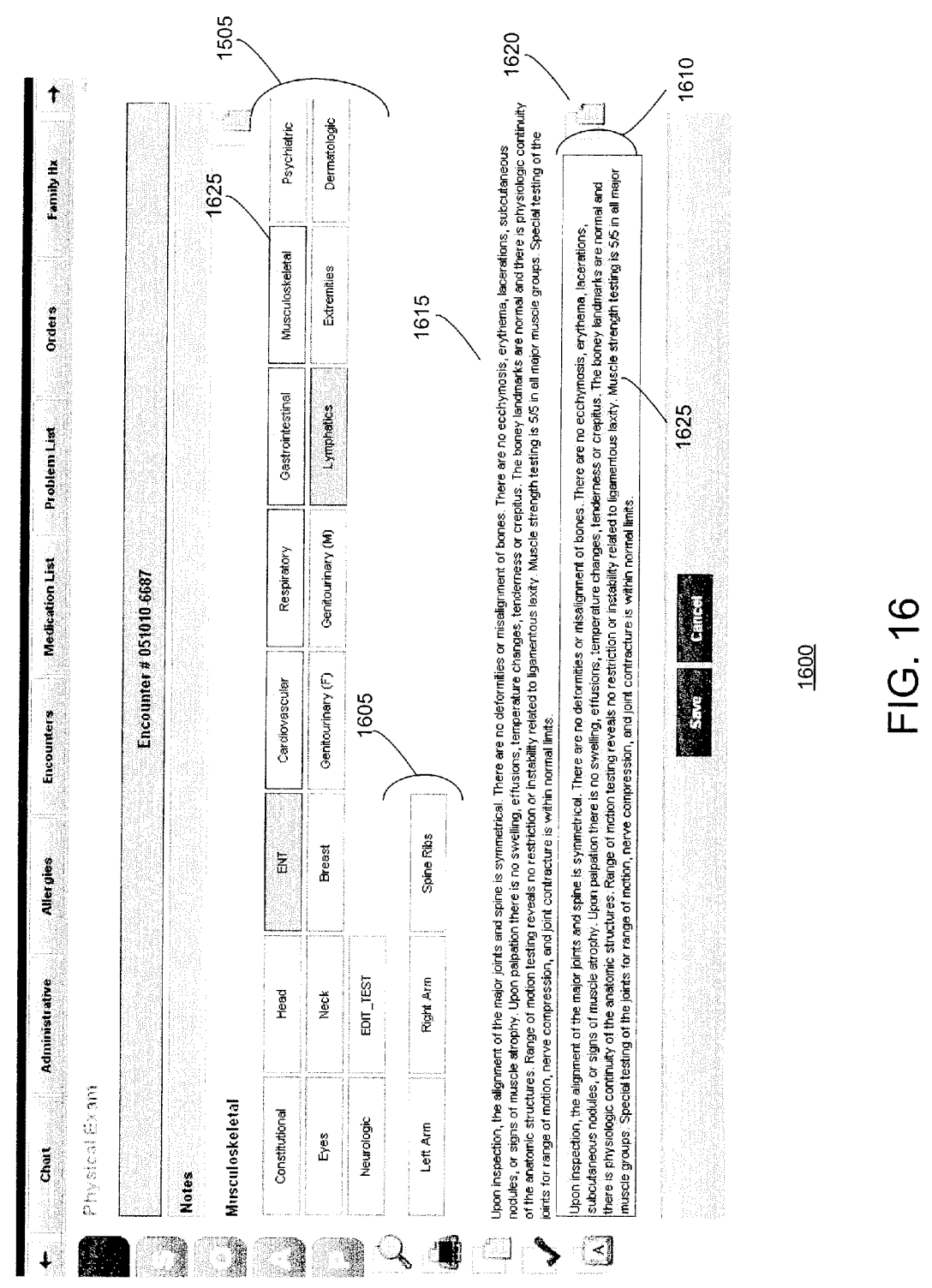

FIG. 16 illustrates a representative screen display 1600 of an interface for entering data associated with a musculoskeletal system of the patient. The display 1600 is provided in response to the activation of a musculoskeletal button 1625. After the activation of the musculoskeletal button 1625, data relating to a second level of the data hierarchy is presented. The data includes a second level group of buttons 1605; a second level group of touch phrase buttons 1610; a text summary 1615; and a note icon 1620. The second level group of touch phrase buttons 1610 consists of a touch phrase button 1625, which is a representative embodiment of a touch phrase button as discussed with reference to FIGS. 3 through 6. The first level of buttons 1505 also remain visible and enabled. The second level group of touch phrase buttons 1610 includes the touch phrase button 1625. It should be noted, however, that multiple touch phrase buttons or no touch phrase buttons could be associated with the second level of the data hierarchy. Activating the touch phrase button 1625 changes the state of the button as described with reference to FIG. 5. The text of the touch phrase button 1625 may then be used in generating of a report. Such activation allows the medical professional to quickly record data without requiring the medical professional to manually write or record patient data.

The text summary 1615 includes a text summary based upon the touch phrase buttons in the second level group of touch phrase buttons 1610. In FIG. 16, the text summary 1615 is a concatenation of the text of all touch phrase buttons from the second level group of touch phrase buttons 1610 that are in a particular state. The text summary 1615 may also be a concatenation of the text of all touch phrase buttons that are not in a particular state. In addition, the text summary 1615 may be truncated or otherwise edited to shorten the length of the text summary 1615.

Each touch phrase button has a note icon 1620 associated with the touch phrase button. The note icon 1620 is used to enter free form data associated with a touch phrase button. The note data may be associated with a touch phrase button regardless of the touch phrase button's state. In an alternative implementation, the note data is associated with a particular state of the touch phrase button. In this alternative implementation, separate note data can be associated with each state of a particular touch phrase button.

Figure 17:
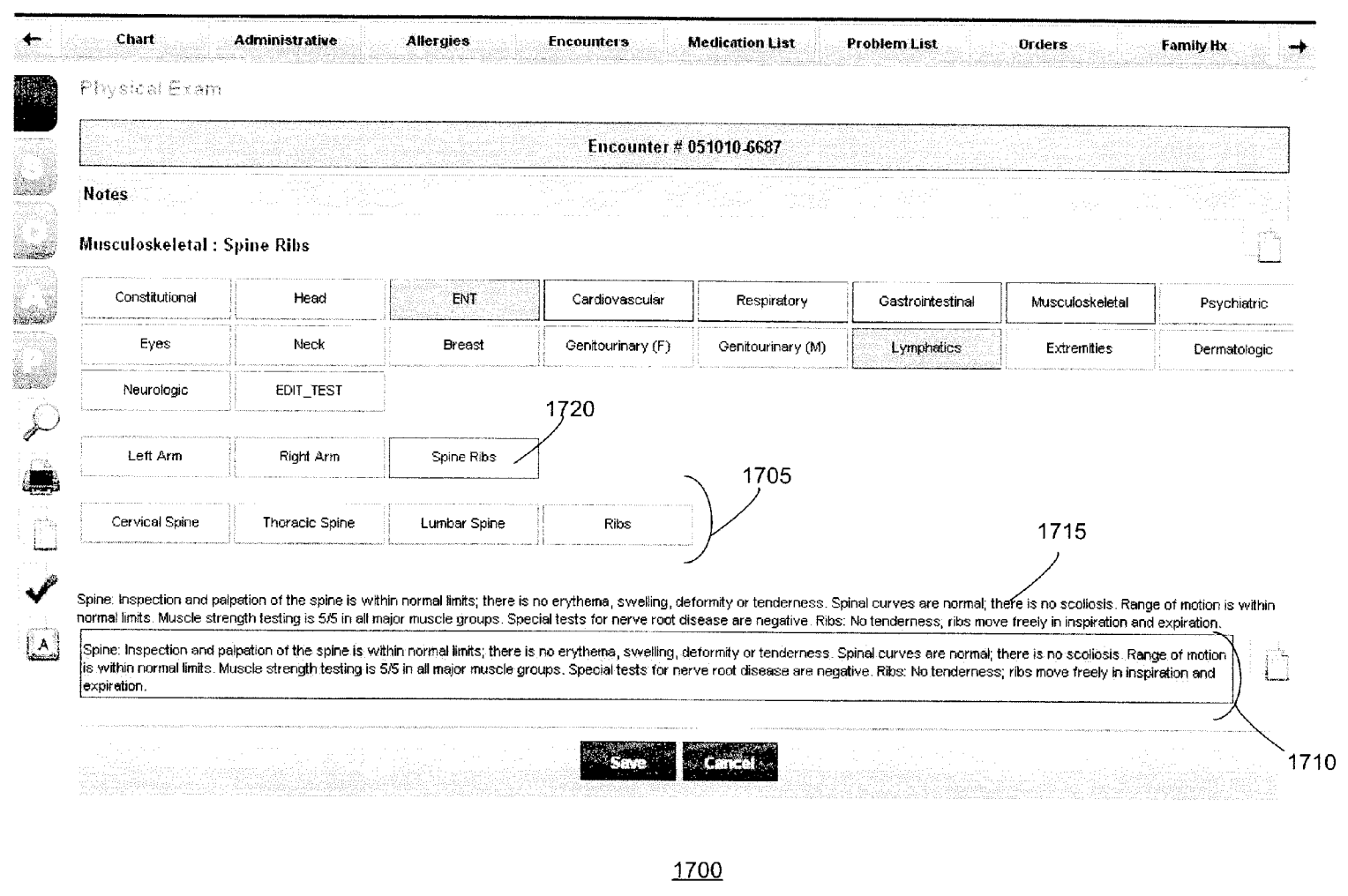

FIG. 17 illustrates a representative screen display 1700 of an interface for entering data associated with a third level of the data hierarchy. The display 1700 is presented in response to a spine ribs button 1720 being activated. In response to the spine ribs button 1720 being activated, a third level group of buttons 1705 is presented along with a third level group of touch phrase buttons 1710. In response to the spine ribs buttons 1720 being activated, the second level group of touch phrase buttons 1610 is no longer shown. In another implementation, the second level of touch phrase buttons 1610 continues to be shown. FIG. 17 also shows a text summary 1715 of the third group of touch phrase buttons. In the illustrated embodiment, the text summary 1615 of the second group of touch phrase buttons is not shown. In an alternative implementation, the text summary of higher related levels of the data hierarchy continues to be shown.

Figure 18:
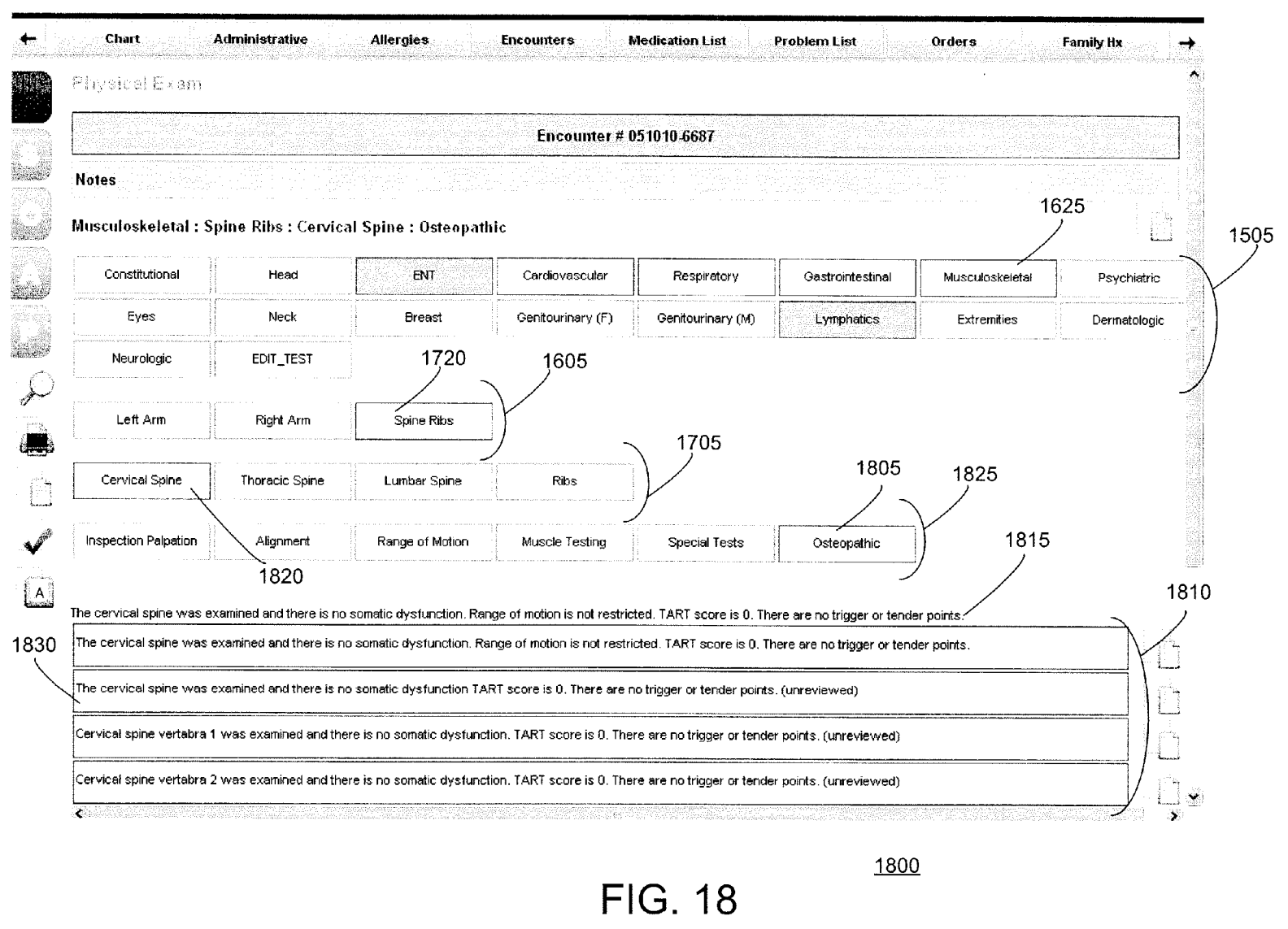

FIG. 18 illustrates a representative screen display 1800 of an interface for entering data associated with an osteopathic level of the data hierarchy. In this illustrative embodiment, the osteopathic level is the fourth level of the data hierarchy. As such, the display 1800 includes a first level group of buttons 1505, a second level group of buttons 1605, a third level group of buttons 1705, and a fourth level group of buttons 1825. In the illustrated example, the osteopathic level is reached after the activation of the musculoskeletal button 1625, the spine ribs button 1705, the cervical spine button 1720 and the osteopathic button 1805. In response to the activation of the osteopathic button 1805, the fourth group of touch phrase buttons 1810 associated with the osteopathic level is displayed, along with a text summary 1815 of a subset of the osteopathic level's touch phrase buttons 1810. In this embodiment, the subset of touch phrase buttons is the set of touch phrase buttons that are in a non-default state.

Screen display 1800 illustrates that the osteopathic level in the data hierarchy is the last navigable level as illustrated by a lack of buttons associated with the osteopathic button. The lack of buttons associated with the osteopathic button restricts the navigation to any level below the osteopathic level.

As demonstrated, the user interface allows navigation through various levels of the data hierarchy. FIGS. 15 through 18 illustrate a single example of navigation through the data hierarchy and are not meant to be limiting. The user interface may be used to navigate levels of a hierarchy that are shallower or deeper than the levels illustrated in the figures.

Figure 19:
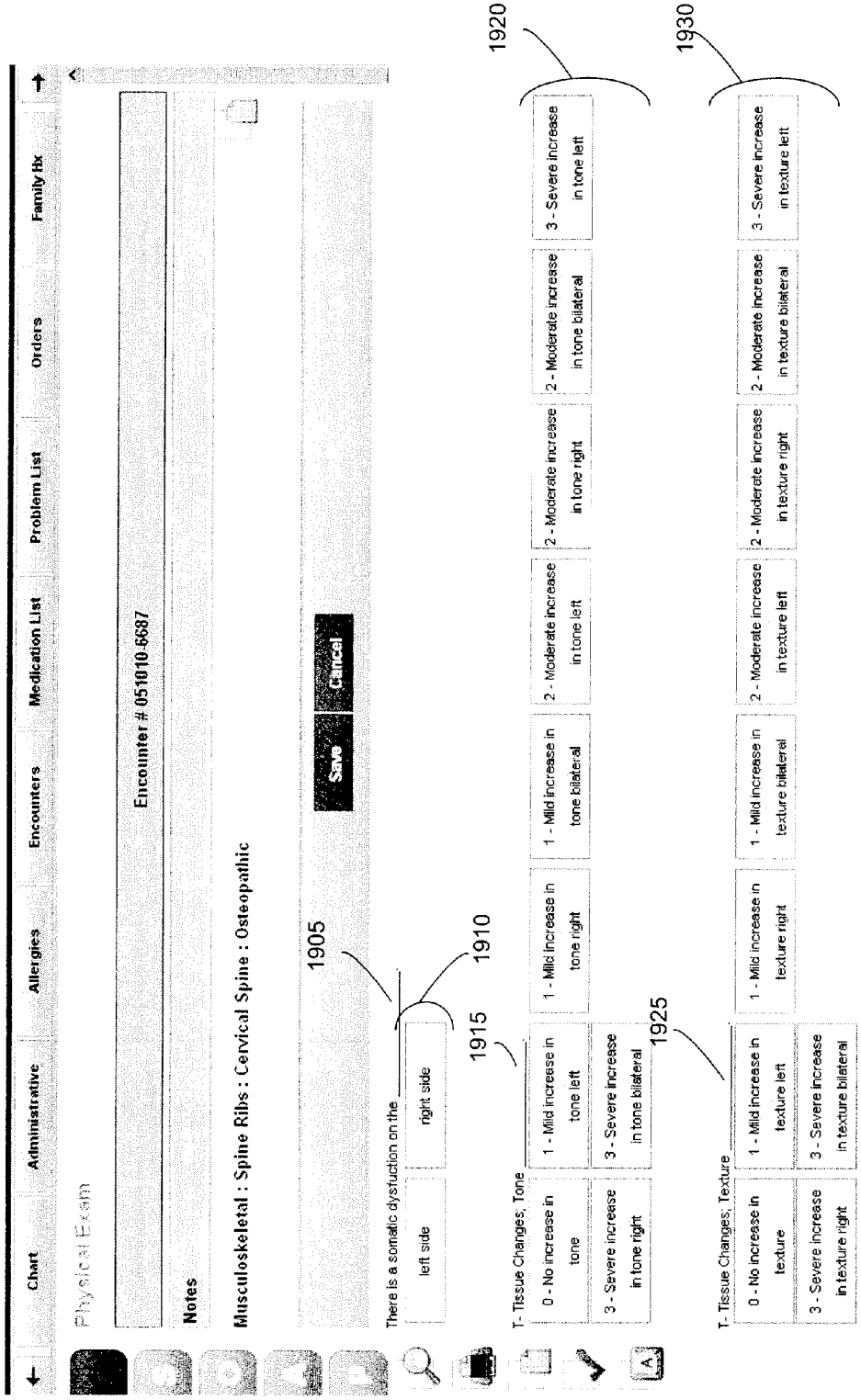
FIG. 19 is a representative screen display for associating data with a touch phrase button.

Touch phrase buttons comprising the fourth group of touch phrase buttons 1810 may have data associated with one or more of the touch phrase buttons. A representative example of associating data with a touch phrase button 1900 is illustrated in FIG. 19, and is a representative embodiment of the touch phrase button 1830 having additional data associated with the touch phrase button as described with reference to FIG. 5. After activating the touch phrase button 1830 into a state that requires additional data, the representative screen display 1900 is displayed. The screen display 1900 is used for entering data associated with the touch phrase button 1830. The screen display 1900 is configurable and may differ based upon an associated touch phrase button and the associated touch phrase button's state. Elements of the display 1900 that are configurable include texts 1905, 1915, and 1925. The texts 1905, 1915, and 1925 not only provide context for groups of buttons 1910, 1920, and 1930, but may also be used in generating a report. The texts 1905, 1915, and 1925 can be configured based upon the preferences of the medical professional.

Figure 20:
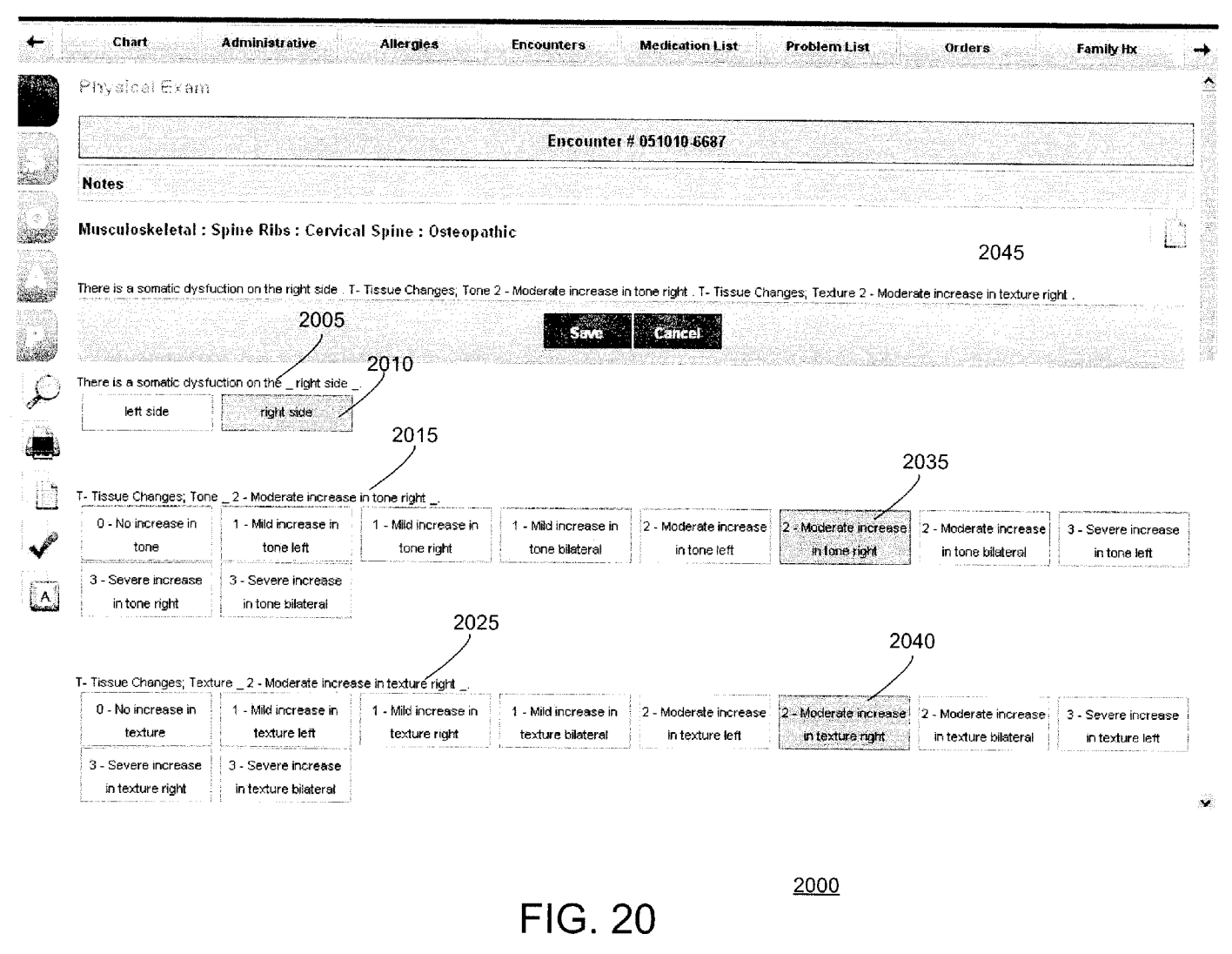

FIG. 20 is a representative screen display 2000 of screen display 1900 after the medical professional has entered the additional data associated with the touch phrase button 1830. As illustrated, button 2010 was activated to indicate that there was a somatic dysfunction on the patient's right side. Based upon this input, the text 2005 was updated to reflect the location of the somatic dysfunction. In addition buttons 2035 and 2040 were also activated, and texts 2015 and 2025 were also updated accordingly. The updated texts 2005, 2015, and 2025 can be used in generating various reports of the electronic health record application. Text 2045 provides an indication of how the texts 2005, 2015, and 2025 are used in the patient report.

After finalizing data input on screen display 2000, the electronic health record application may display representative screen display 2100. Screen display 2100 is the screen display 1800 updated to reflect the changes entered as described with reference to FIG. 20. Based upon the state of touch phrase button 2105 and the additional data associated with touch phrase button 2105, various elements of the screen display are updated. For instance, the buttons 1625, 1720, 1820, and 1805 have had their appearances changed as indicated by the buttons 1625, 1720, 1820, and 1805 appearing with cross hatching. The appearance of the buttons 1625, 1720, 1820, and 1805 may change their background color, font color, or other visual element based upon the state of the touch phrase button 2105 and the additional data associated with touch phrase button 2105. The appearance of touch phrase button 2105 has also changed based upon the touch phrase button's state and the additional data associated with touch phrase button 2105. In addition to the appearance of the buttons 1625, 1720, 1805, and 1820 changing, the text 1815 associated with the fourth level group of touch phrase buttons 1810 is also updated accordingly.

After the medical professional enters all of the patient's relative information associated with the data hierarchy, a physical examination summary 2205 regarding the physical examination can be generated. FIG. 22 is a representative screen display 2200 of a physical examination summary. Generating the physical examination summary 2205 is a representative embodiment of generating a report as described with reference to FIG. 7. The physical examination summary 2205 is automatically generated based upon the physical examination data entered previously by the medical professional as described with reference to FIGS. 15 through 21. For instance, the text 2210 is based upon the data input as described with respect to FIG. 21. Generating the physical examination summary 2205 saves the medical professional from having to write up the examination summary while examining the patient. One advantage of this automatic generation of the examination summary 2205 is that the medical professional can spend more time focusing on the patient, instead of writing the patient's data manually in a file during the physical examination.

Figure 23:
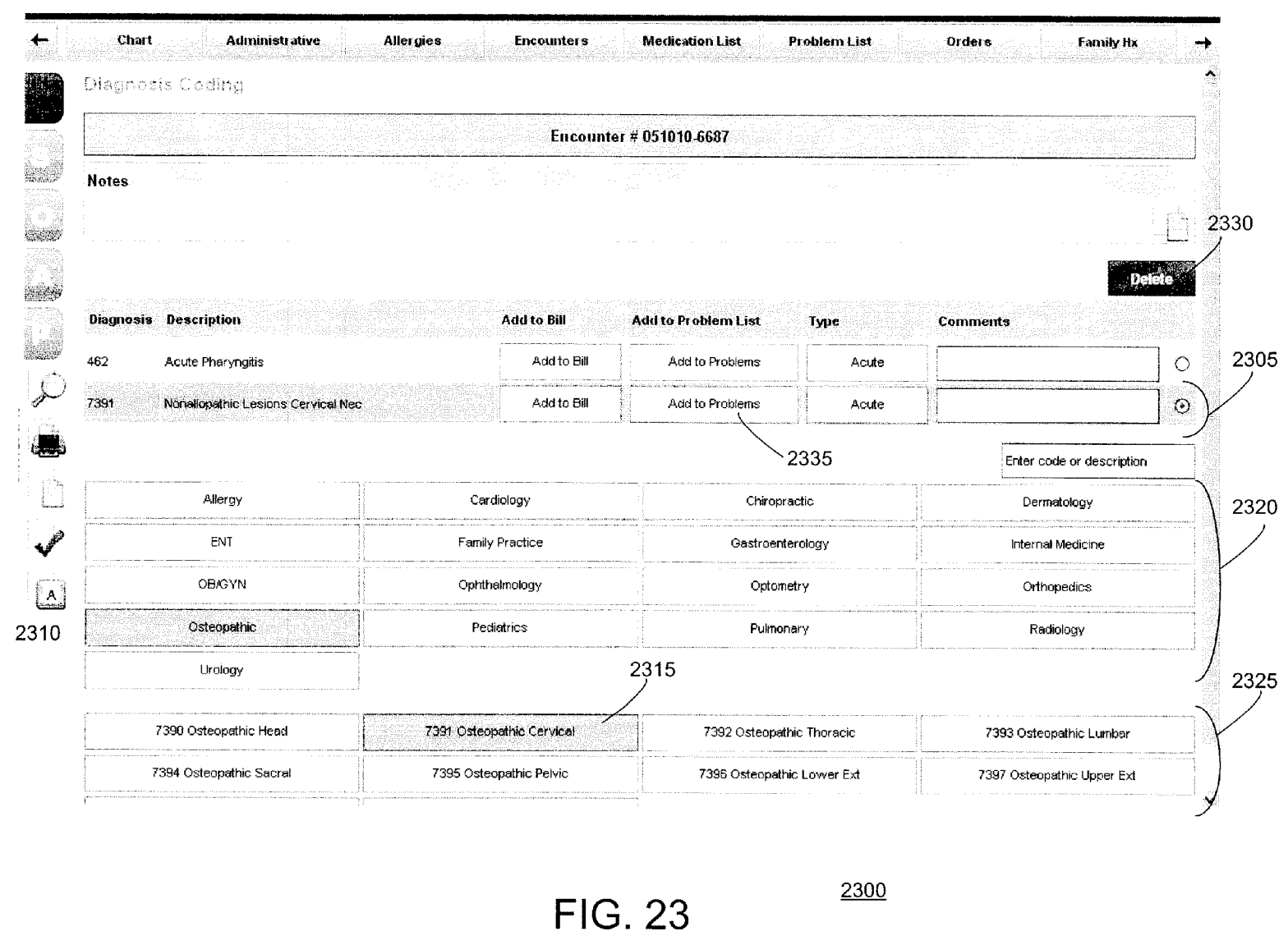

After the medical professional reviews the physical examination summary 2205, the patient examination transitions to the assessment phase. FIG. 23 illustrates a representative diagnosis screen display 2300. A diagnosis is entered into by activating a button from a first group of buttons 2320. In this example, osteopathic button 2310 is activated. In response to the osteopathic button 2310 being activated, a second group of buttons 2325 is displayed. In this representative example, an osteopathic cervical button 2315 is activated. After the osteopathic cervical button 2315 is activated, a row corresponding to this diagnosis 2305 is created. The diagnosis can be added to a patient's problem list by activating button 2335. Once the diagnosis has been added to the problem list, it can be removed by activating button 2335 again. The diagnosis may also be added to the patient's problem list automatically when the row corresponding to the diagnosis 2305 is created. Diagnostic rows can be deleted by activating a radio button associated with a diagnostic row, and then activating the delete button 2330.

After the medical professional completes entering relevant diagnostic codes, the patient examination moves into a final planning portion. Coding each procedure performed during the patient examination is shown in a representative procedure coding screen display 2400 of FIG. 24. Row 2405 illustrates a procedure coding of an office visit of the patient. In this example, the patient is an established patient. An add to bill button 2435 can be activated to add a procedure to the patient's bill. The row 2405 was generated by the activation of an evaluation and management button 2415 that is located in a first group of buttons 2410. After the activation of button 2415 a second group of buttons 2420 is displayed. Row 2405 is generated as a result of the activation of an established patient button 2425.

The electronic health record application can be integrated with the claims management application to generate a claim associated with entered diagnostic and procedure codes. The diagnostic and procedure codes and other data can be transmitted to the claims management applications via the healthcare management framework when a generate patient management system billing button 2430 is activated.

Figure 25:
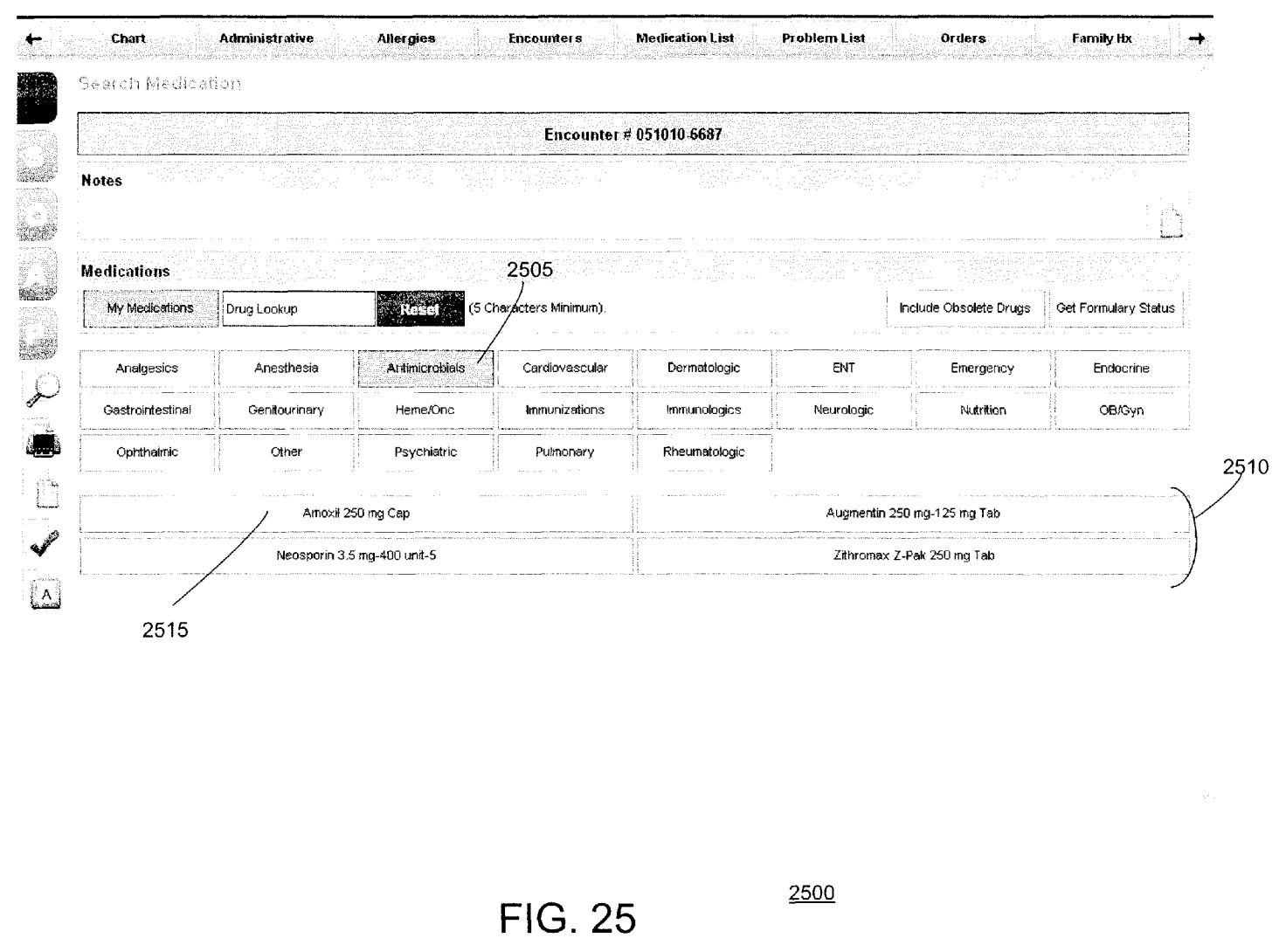
Figure 26:
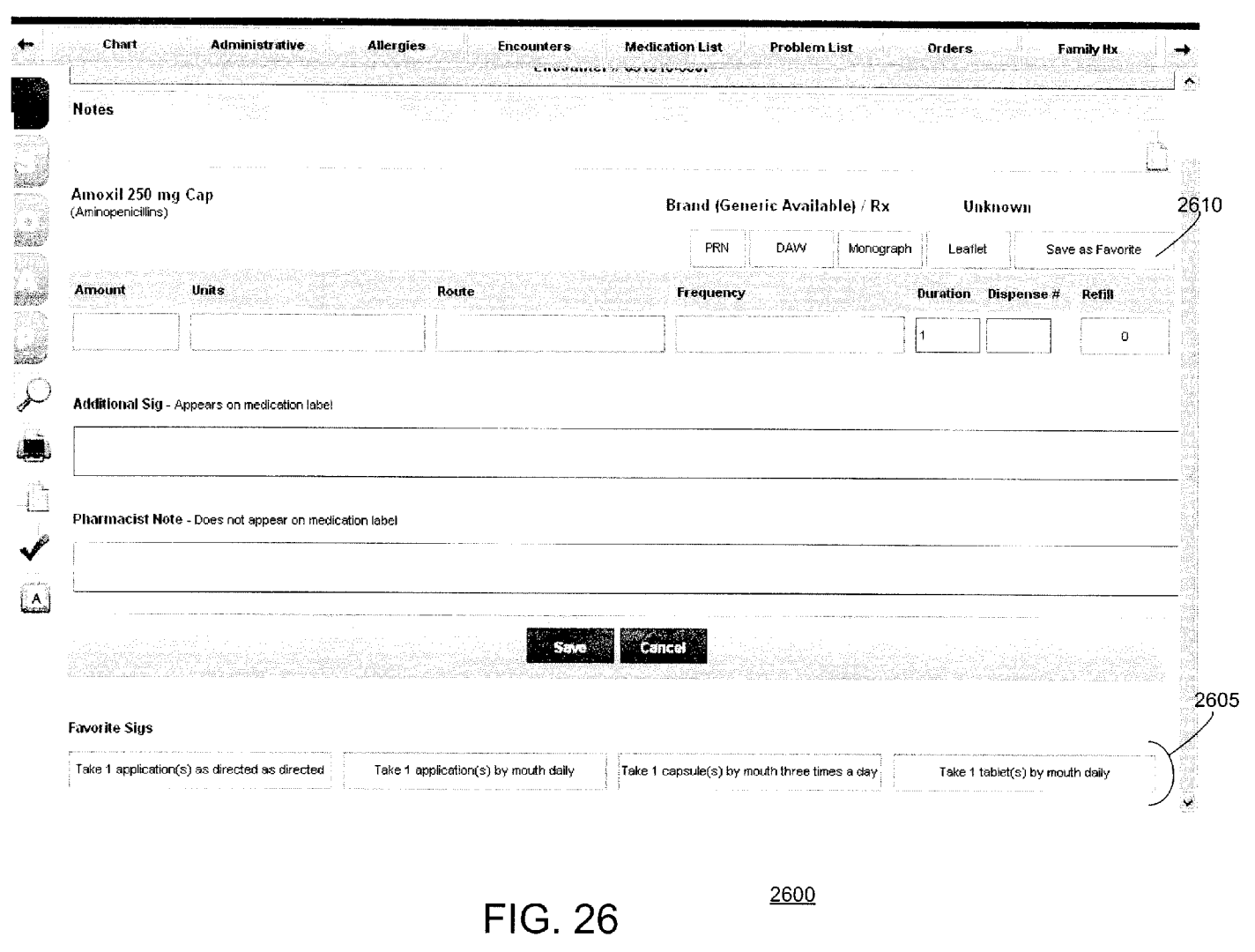

Once relevant procedure codes have been entered, the medical professional may then prescribe medication to the patient. FIG. 25 is a representative medication search screen display 2500. In response to activating an antimicrobials button 2505, a group of buttons 2510 is displayed. The group of buttons 2510 corresponds to common prescriptions of antimicrobials prescribed by the medical professional. The group of buttons 2510 is configurable based upon the medical professional's preferences. The activation of a button from the group of buttons 2510 updates the patient's electronic chart with the selected prescription. FIG. 26 is a representative screen display 2600 displayed in response to an Amoxil 250 mg cap button 2515 being activated. The screen display 2600 allows the medical professional to activate one or more signatures from a group of previously saved signatures 2605. In addition, the medical professional can save a prescription as a favorite by activating button 2610. A favorite prescription may then be displayed in the group of buttons 2510.

Figure 27:
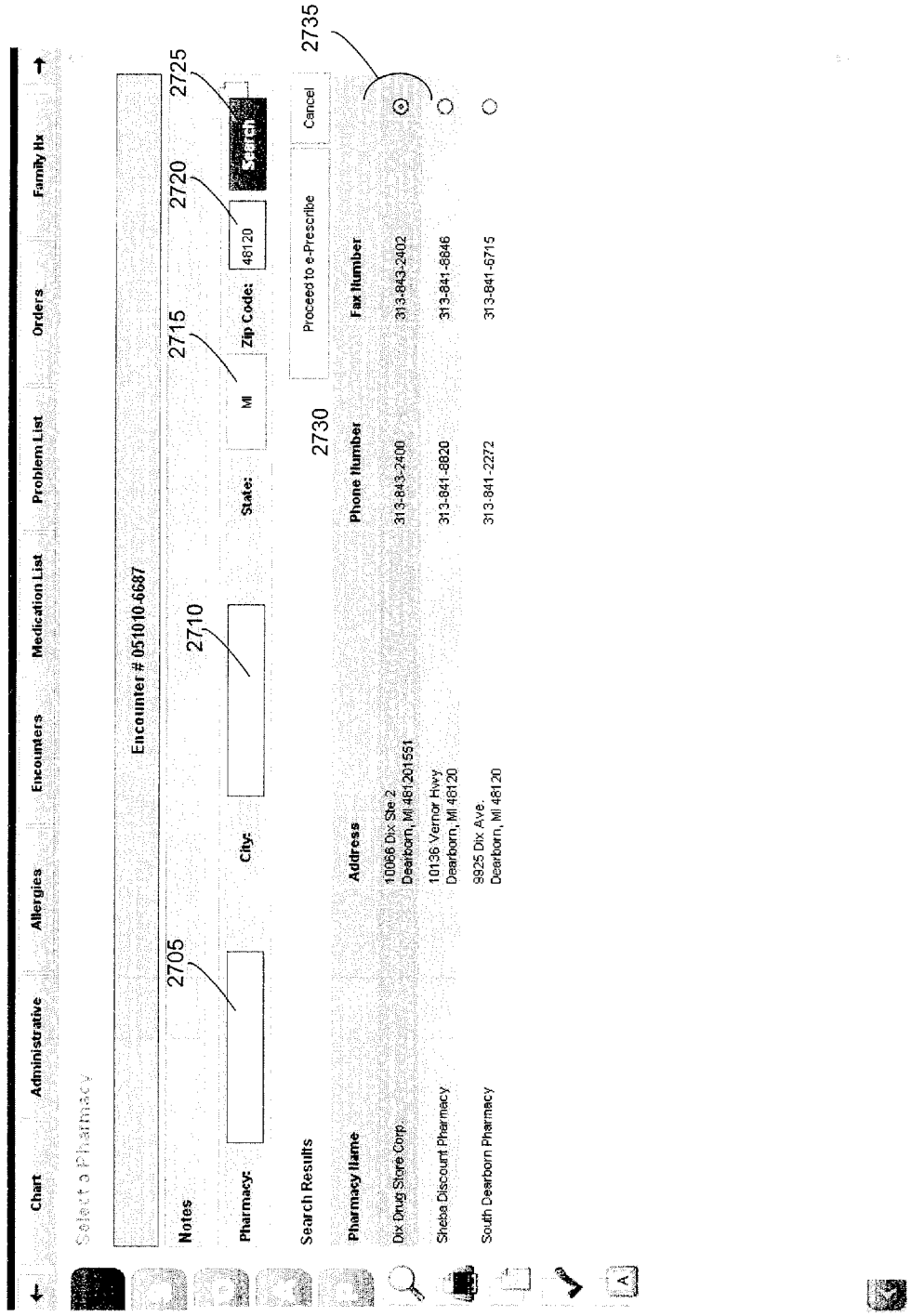
FIG. 27 is a representative pharmacy selection screen display.

Once information regarding a prescription is entered, the medical professional may then select a pharmacy to fulfill the prescription. FIG. 27 provides a representative pharmacy selection screen display 2700. The electronic health record application allows the medical professional to search known pharmacies. Pharmacies can be searched based upon a number of criteria including, but not limited to, name, city, state, and zip code. The medical professional enters the appropriate criteria in a name text box 2705, a city text box 2710, a state drop down list 2715, and a zip code text box 2720. A pharmacy search is initiated by the activation of a search button 2725. The pharmacy search returns a list of pharmacies 2735. From this list a pharmacy can be selected. Once a pharmacy is selected, prescription data can then be sent to the pharmacy to initiate an e-prescription process by the activation of a e-prescribe button 2730.

Figure 28:
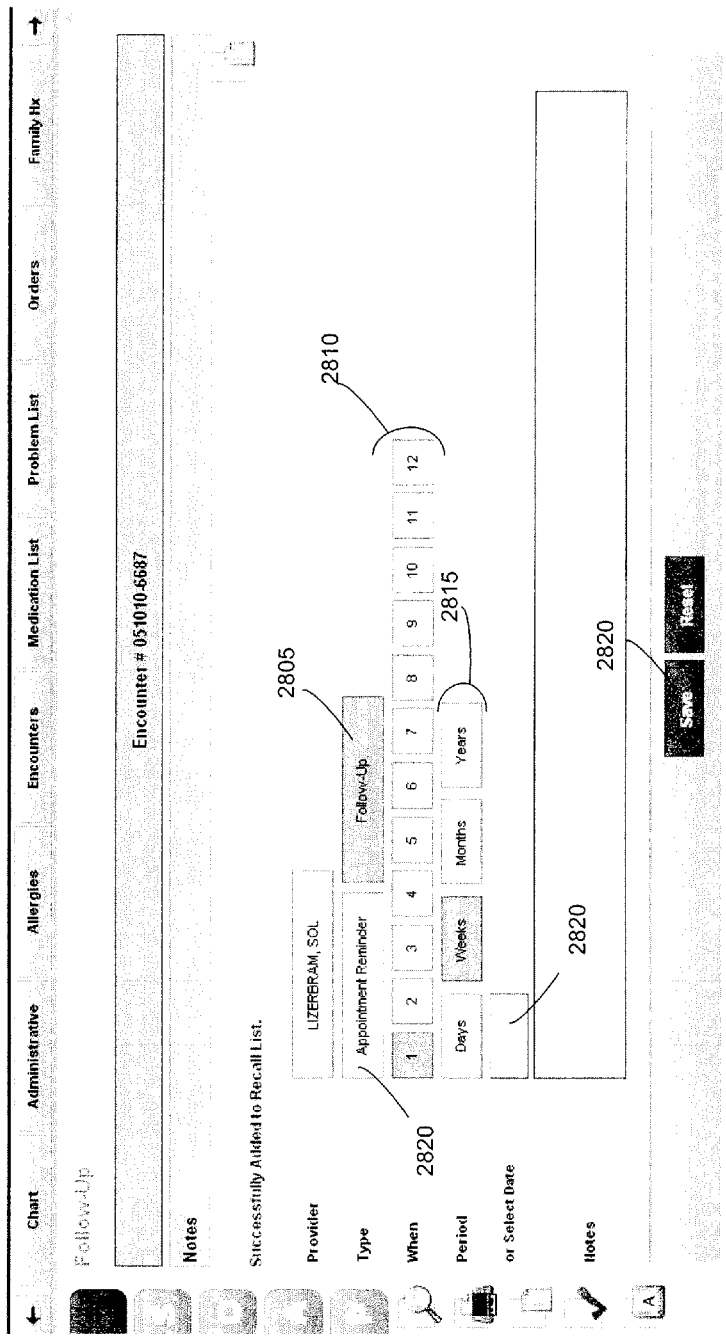
FIG. 28 is a representative follow-up screen display.

Another illustrated feature of the electronic health record application is the ability to schedule follow-up appointments or appointment reminders. FIG. 28 is a representative follow-up screen display 2800. A follow-up can be scheduled by the activation of a follow-up button 2805. The date of the follow-up is then selected based upon the activation of the when button 2810 and the period button 2815. Alternatively, a specific date could be entered in the text box 2820. The specific date could also be entered using a calendar selection tool. After a save button 2825 is activated, the follow-up appointment can then automatically be scheduled by the electronic health record application. Saving of the follow-up appointment may be through integration with the patient management application. An appointment reminder can also be created using the display elements illustrated in the screen display 2800. An appointment reminder button 2830 would be activated instead of the follow-up button 2805. Selecting a date for the appointment reminder would be accomplished in a similar manner as selecting a date for the follow-up appointment.

Figure 29:
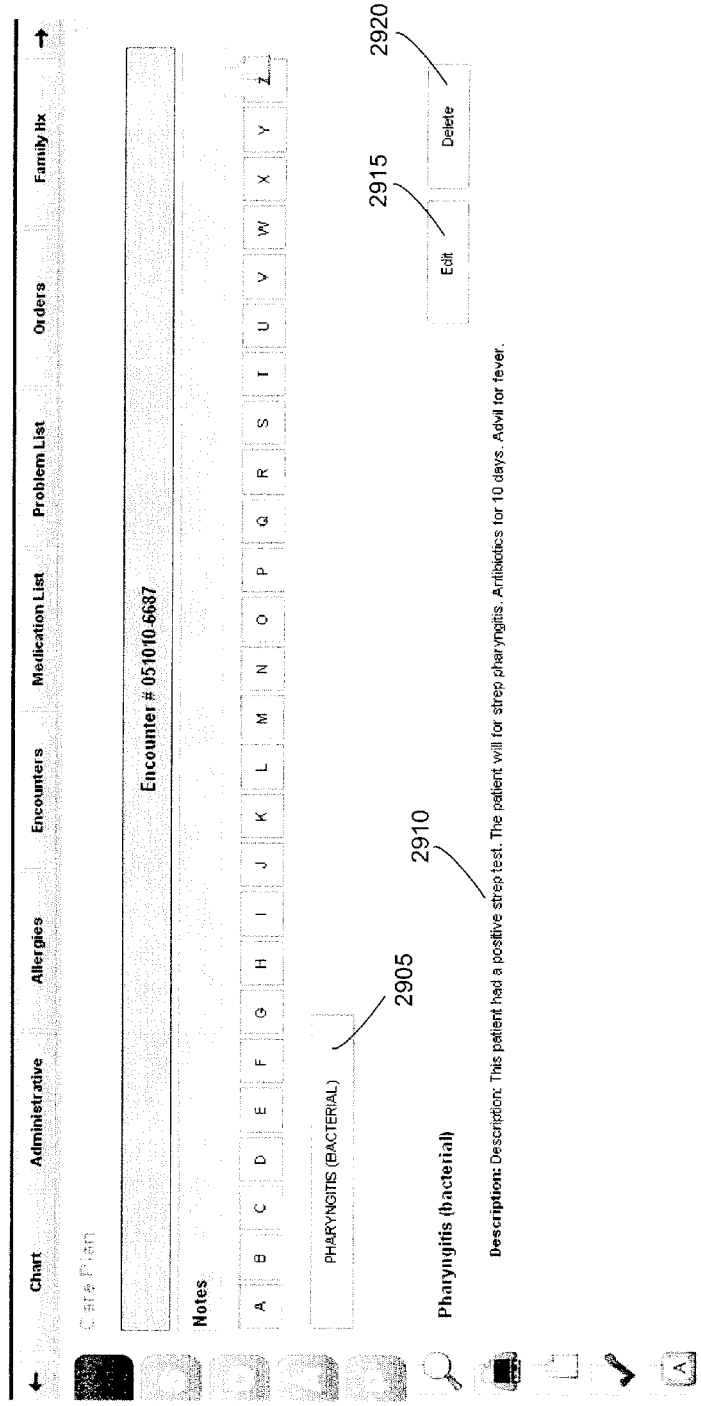
FIG. 29 is a representative care plan screen display.

The electronic health record application also allows the medical professional quickly to construct a care plan for the patient. FIG. 29 is a representative care plan screen display 2900. The medical professional can search for care plan instructions to provide to the patient based upon the examination. Activating a pharyngitis button 2905 displays instructions 2910 that can be provided to the patient. The notes can be edited with activation of an edit button 2915 or deleted from the patient's record with activation of a delete button 2920.

Figure 30:
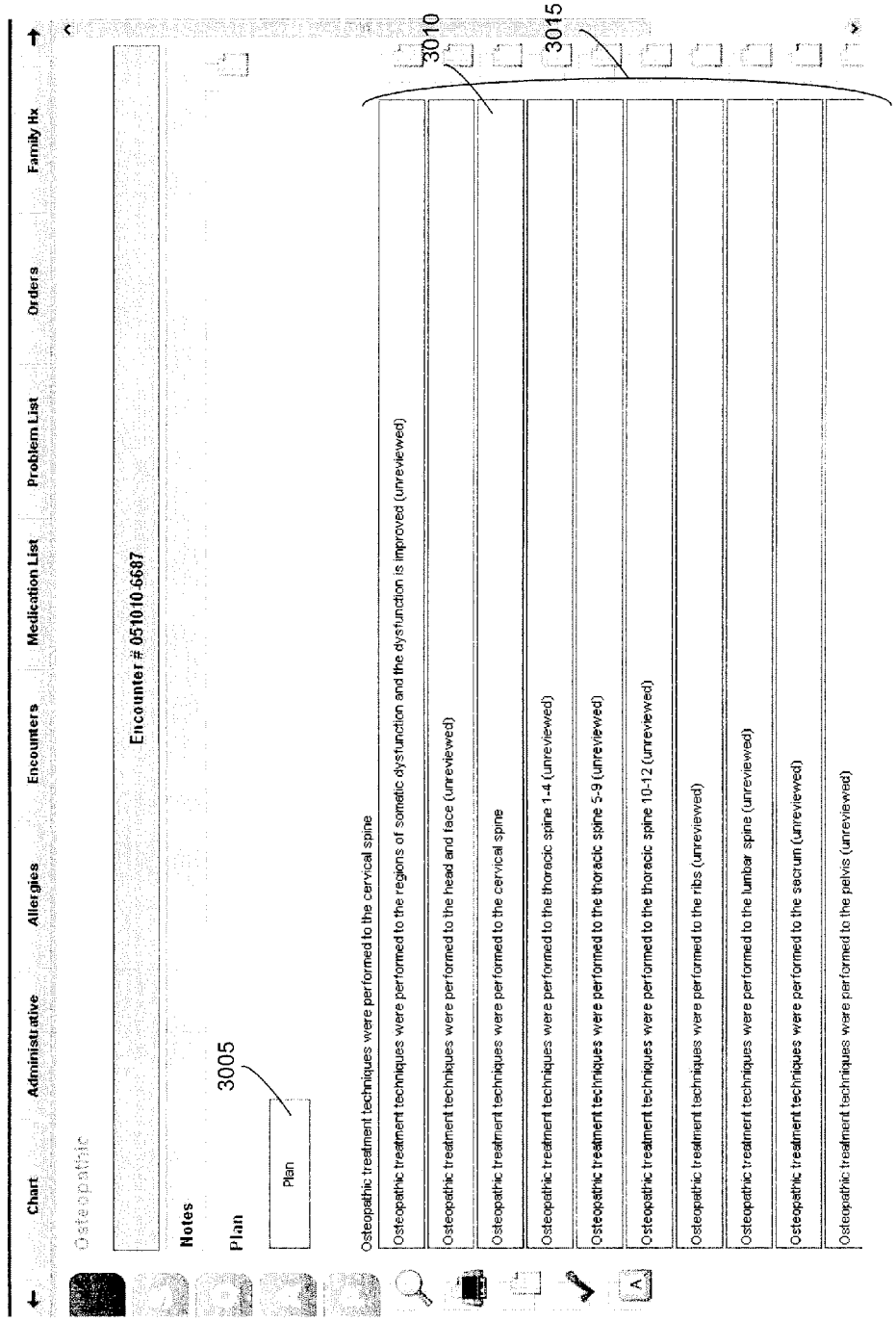
FIG. 30 is a representative osteopathic plan screen display.
Figure 31:
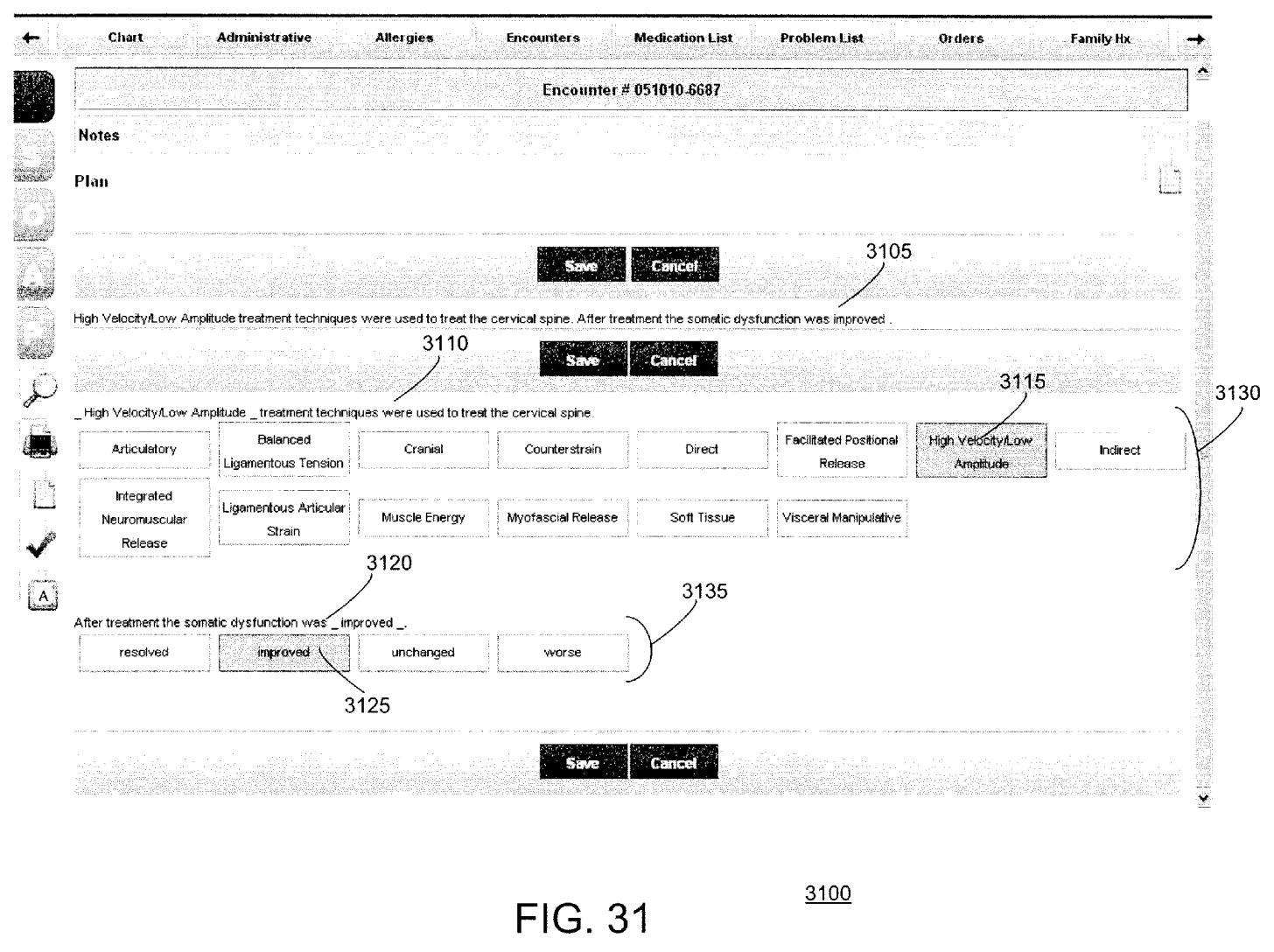

The medical professional can also record and provide the patient with an osteopathic plan. FIG. 30 is a representative osteopathic plan screen display 3000. A group of touch phrase buttons 3015 lists possible plan items. As described with respect to FIG. 5, a touch phrase button can be associated with additional data. In the illustrative example, activating touch phrase button 3010 causes additional data to be collected. FIG. 31 is a representative osteopathic data entry screen display 3100. A group of buttons 3130, corresponding to various types of treatment techniques, is displayed. Activation of one of these buttons updates a text value 3110. In the representative example, a treatment consisted of a high velocity/low amplitude treatment technique. Accordingly, when button 3115 is activated, the text value 3110 is updated. Text 3120 corresponds to the result of the treatment. A second group of buttons 3135 provides the possible results of the treatment. In the representative screen display 3100, an improved button 3125 has been selected, and the text 3120 has been updated accordingly. A text 3105 is also generated based upon both the text 3110 and 3120. Both the group of buttons 3130 and the second group of buttons 3135 are configurable. For instance, additional result buttons could be added to the second group of buttons 3135, or different results buttons could be displayed depending upon which button from the group of buttons 3130 is activated.

Throughout the patient examination, patient data may be input using custom forms. Custom forms include one or more configurable questions. A configurable question may also be in the form of a statement. Questions may be added, deleted, or edited to further increase the efficiency of patient examination, data collection, and health record management. Each question has a text portion, an answer portion, and a notes portion. The text portion includes the text of the question. The answer portion includes at least one answer type, and may include multiple answer types. Each answer type controls how the answer to a question is received. For instance, an answer type may be, but is not limited to, a yes/no answer type which accepts either a yes or no answer. Finally, the notes portion is used to collect any notes associated with the question.

Figure 33:
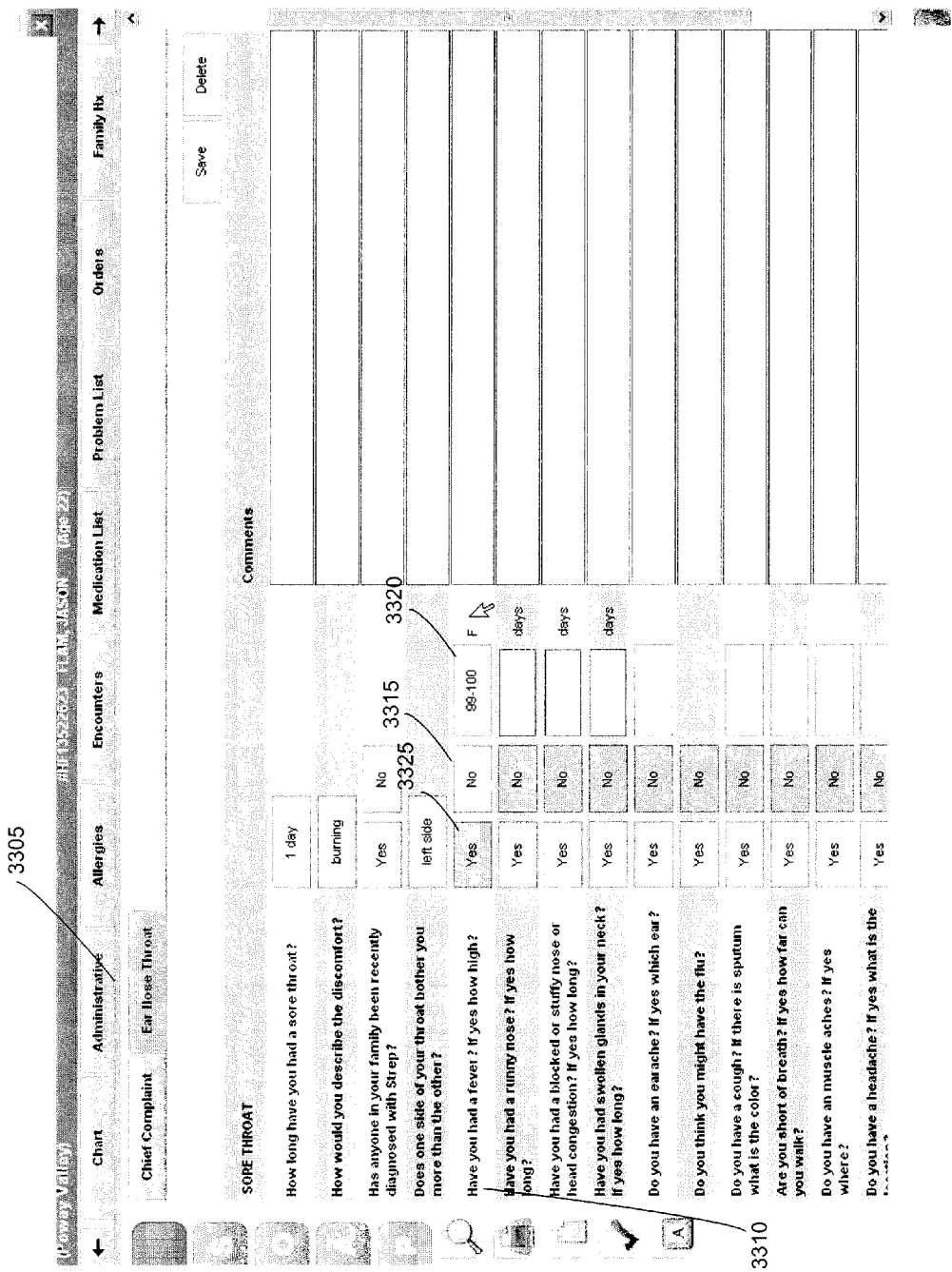
FIG. 33 is a representative custom form screen display.

FIG. 33 is a representative screen display 3300 of a custom form interface for entering patient data relating to a sore throat. Activating the custom Ear Nose Throat tab 3305 activates this form 3300. The form is a custom form, as a user of the representative electronic health record application can configure which questions and allowable answers are displayed. Multiple custom tabs and custom forms may be part of the representative electronic health record application.

Figure 34:
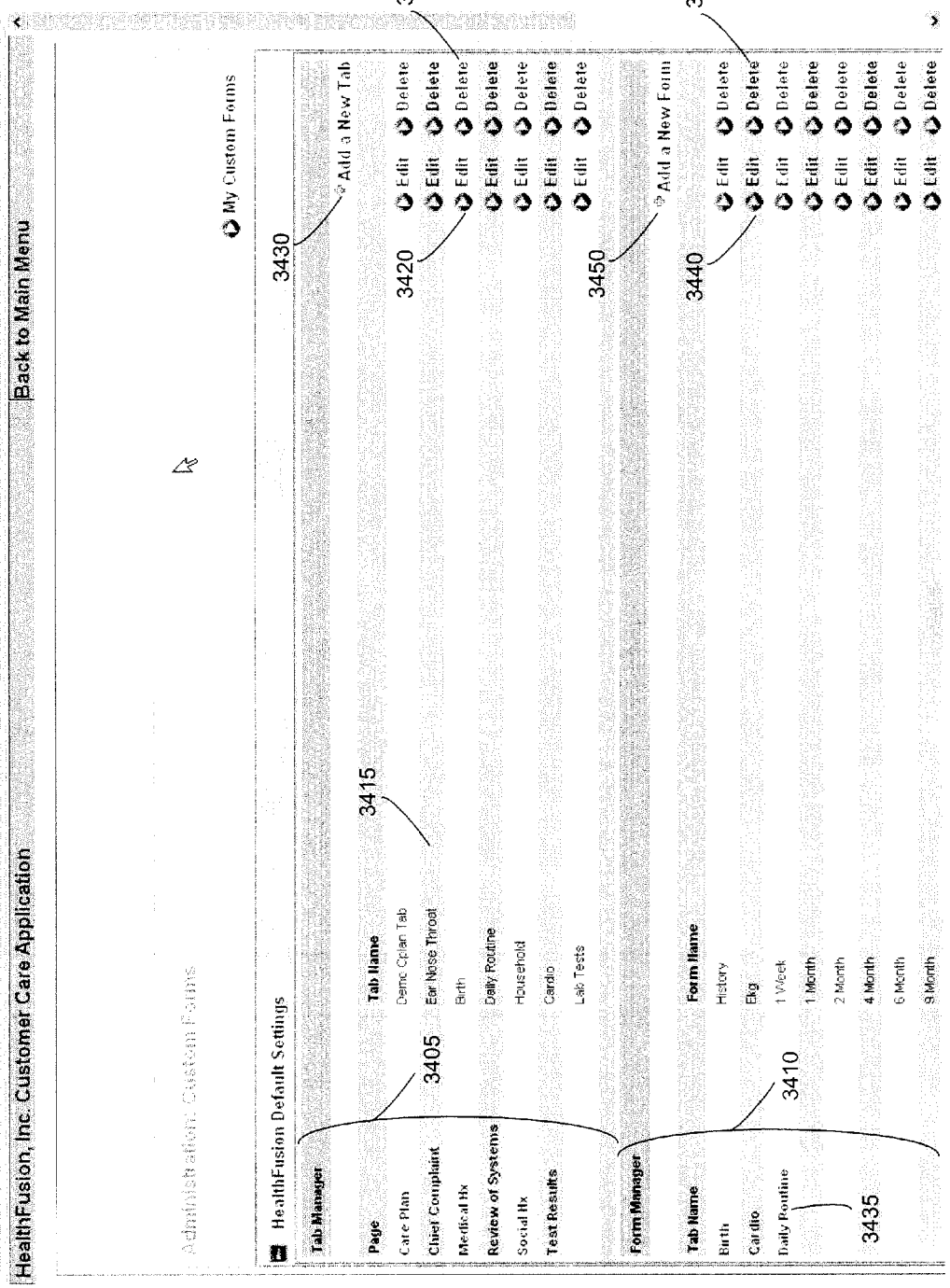
FIG. 34 is a representative custom form and custom tab administration screen display.

FIG. 34 is a representative screen display 3400 of an interface for administration of custom tabs and custom forms. The screen display 3400 includes administration sections for custom tabs 3405 and custom forms 3410. The custom tabs section 3405 provides a list of all custom tabs and the page on which the custom tab is displayed. For example, row 3415 corresponds to the Ear Nose Throat tab 3305 and is displayed on the Chief Compliant page, as illustrated in FIG. 33. An edit button 3420 allows the properties of tab 3305 to be edited. The tab may also be deleted from the application through activation of a delete button 3425.

Figure 35:
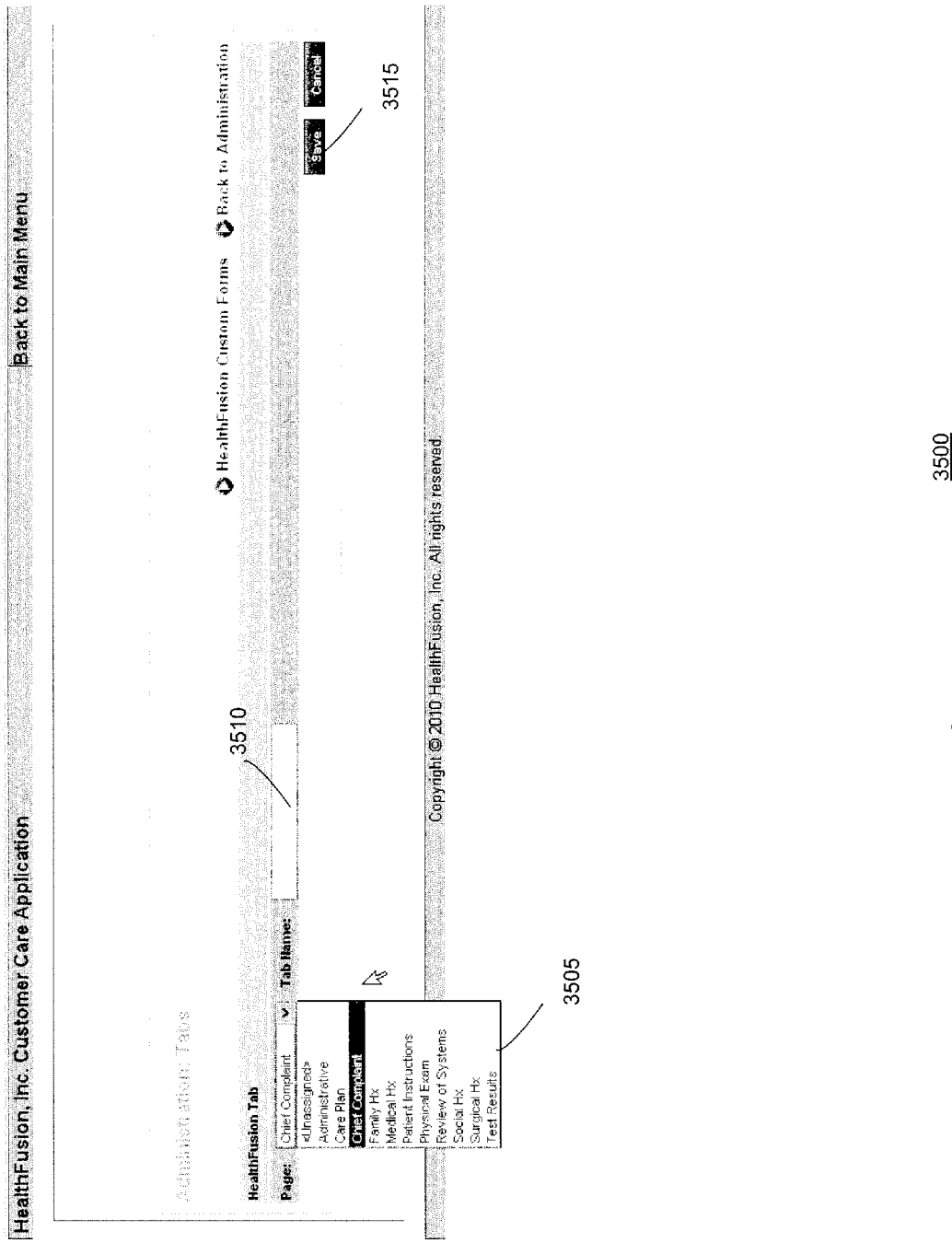
FIG. 35 is a representative screen display for adding a new custom tab.
Figure 36:
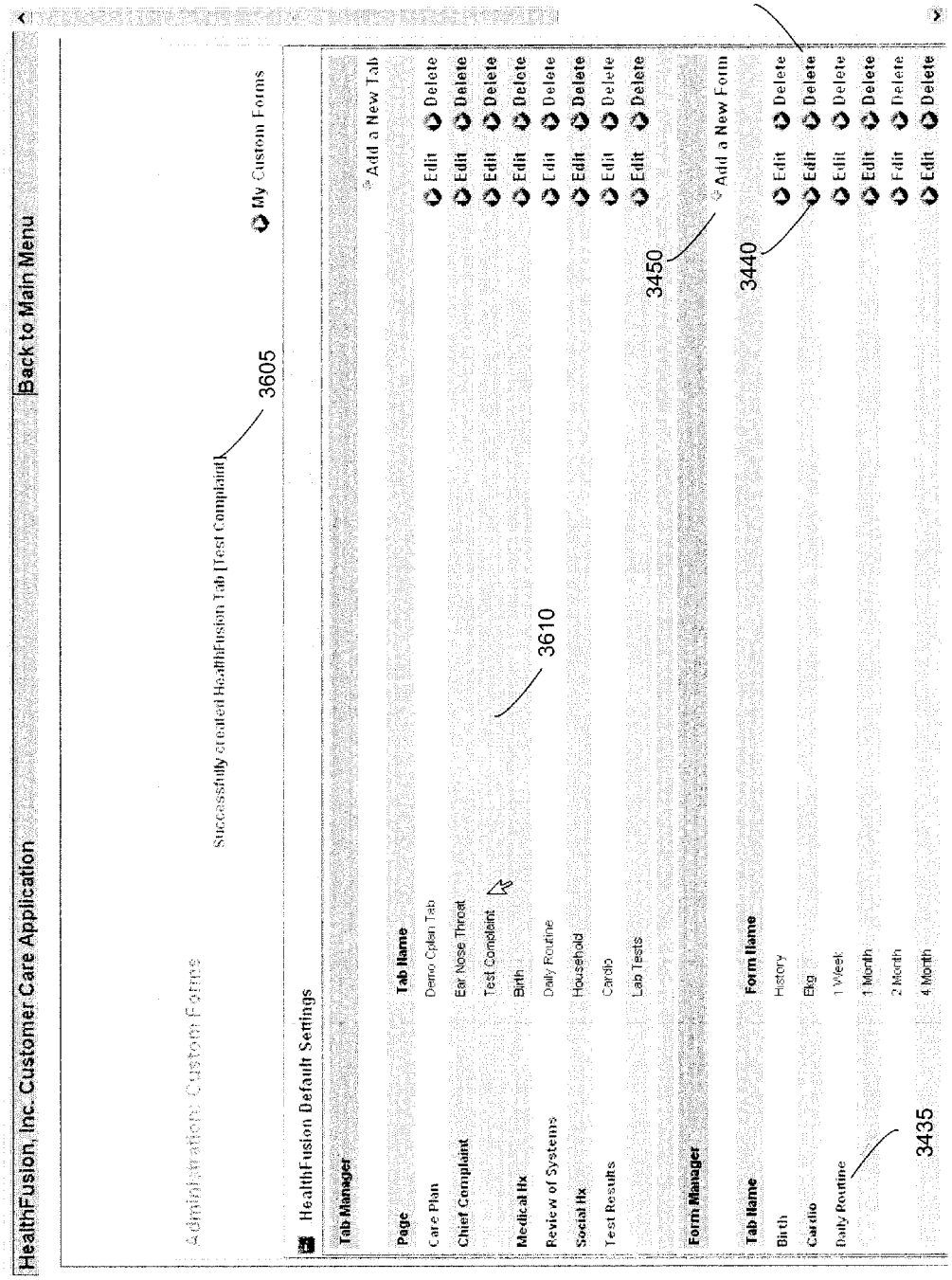
FIG. 36 is a representative screen display showing a successful creation of a custom tab.

New tabs may be added through activating an Add a New Tab button 3430. FIG. 35 is a representative screen display 3500 of an interface for adding a new tab screen. A drop down list 3505 associates a page with the new tab. A page may be selected through other means, such as but not limited to, radio buttons, check boxes, text boxes or selectable items from a list. A text box 3510 allows the tab to be given a name. Creation of the tab occurs after the save button 3515 is activated. FIG. 36 is a representative screen display 3600 showing the successful creation of a custom tab. A message 3605 is displayed indicating that the tab was created. A row 3610 indicates the new tab is added to the associated page. As shown in screen 3600, a page may be associated with multiple tabs. Pages may also have no associated tabs. In this scenario the page is not shown in the administration section for custom tabs 3405.

When a tab is activated, any form associated with the tab is displayed. Multiple forms may be displayed if multiple forms are associated with a particular tab. For instance, the Daily Routine tab 3435 is associated with multiple forms. Forms can be edited or deleted through the use of buttons. As an example, the Ekg form may be edited with the activation of button 3440 or deleted by the activation of button 3445. New forms may be added by activating the Add a New Form button 3450.

Figure 37:
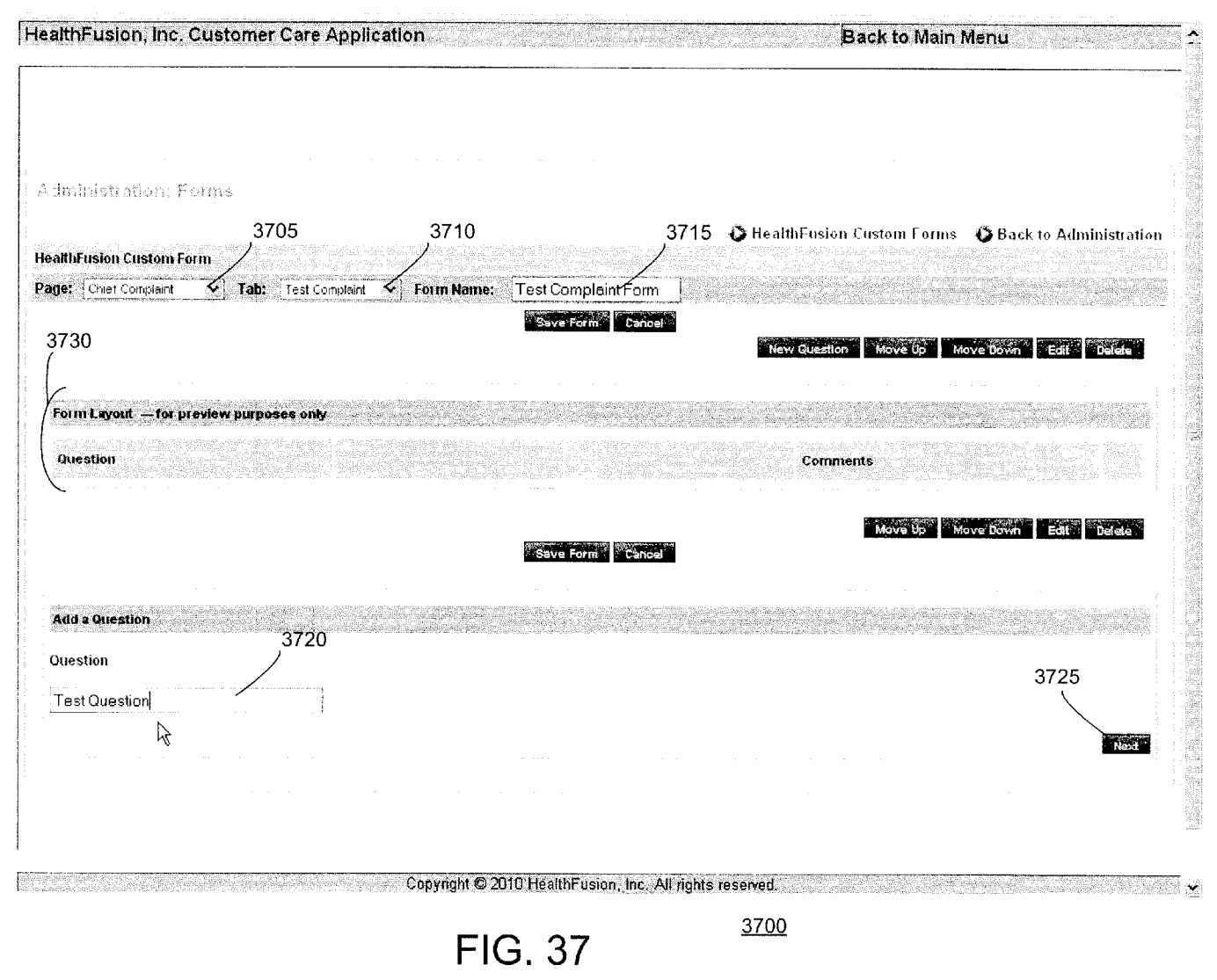

FIG. 37 is a representative screen display 3700 of an interface for adding a new custom form. A custom form is associated with both a page and a tab. The page is selected using a drop down list 3705. Once a page is selected, a tab drop down list 3710 is populated with all of the custom tabs associated with the selected page. Selecting items on this or other representative pages is not limited to the use of drop down list. Items may be selected through other means, such as but not limited to, radio buttons, check boxes, text boxes or items in a selectable list. A form has a name, which may be input through the text box 3715. A custom form includes a list of questions and possible answers. Text of a question may be input using a text box 3720. Activating a next button 3725 adds the text of the question to a form layout section 3730. The form layout section provides a visual preview of the form. Each question is associated with one or more answer types.

Figure 38:
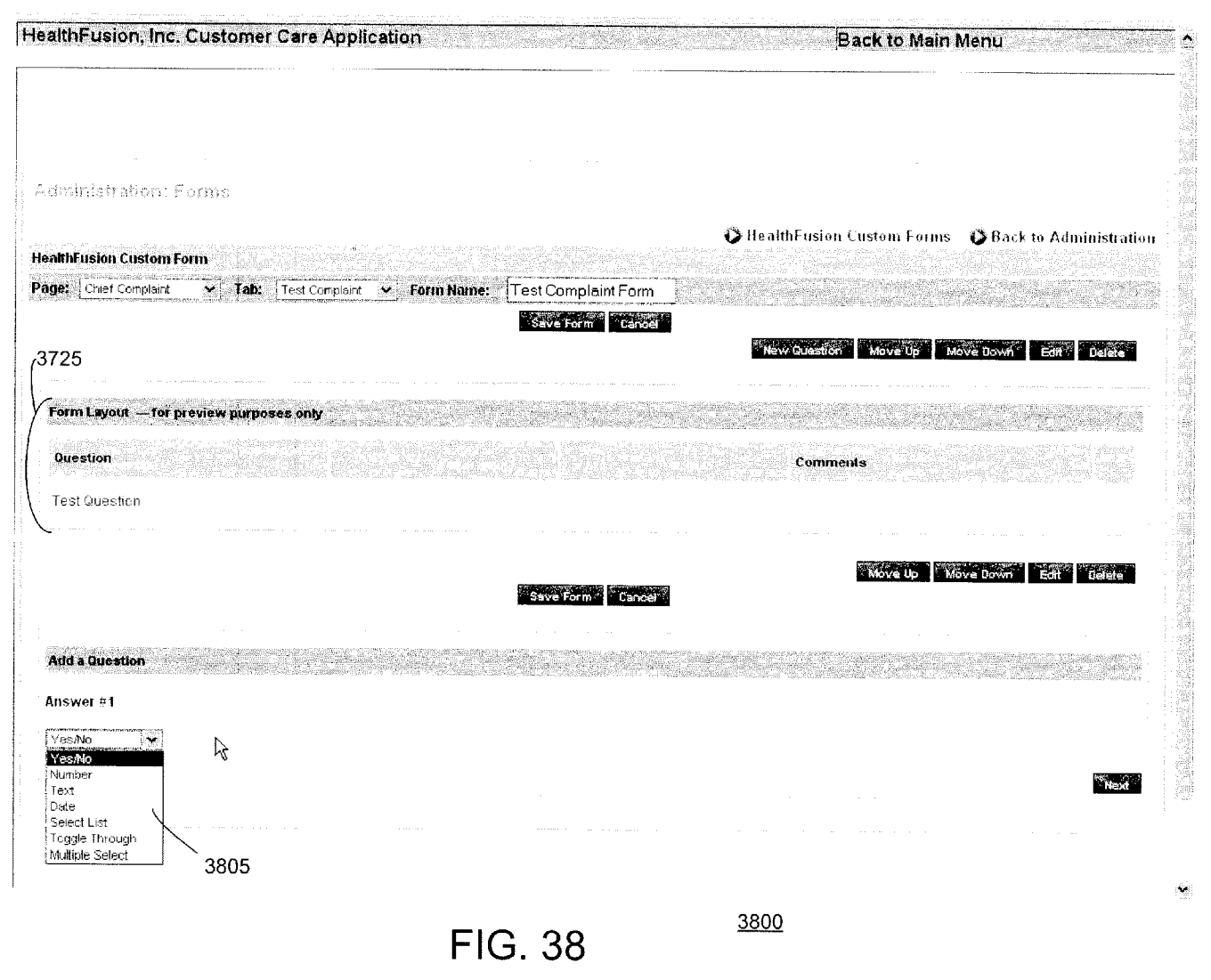

FIG. 38 is a representative screen display 3800 of an interface to select a first answer type for the question. Answer types can be, but are not limited to, a yes/no response, a number, text, a date, a select list, a toggle through, or a multiple select list. A drop down list 3805 may be used to select an answer type for the question. Answer types indicate how a particular answer is input and displayed, and provides validating logic for validating answers. Non-limiting examples of validating logic include ensuring a number is properly received for a number answer type or ensuring that a date is properly received for a date answer type. Answer types may also allow answers to be restricted to a subset of possible values. For example, a number answer type may only accept numbers in a particular range.

Figure 39:
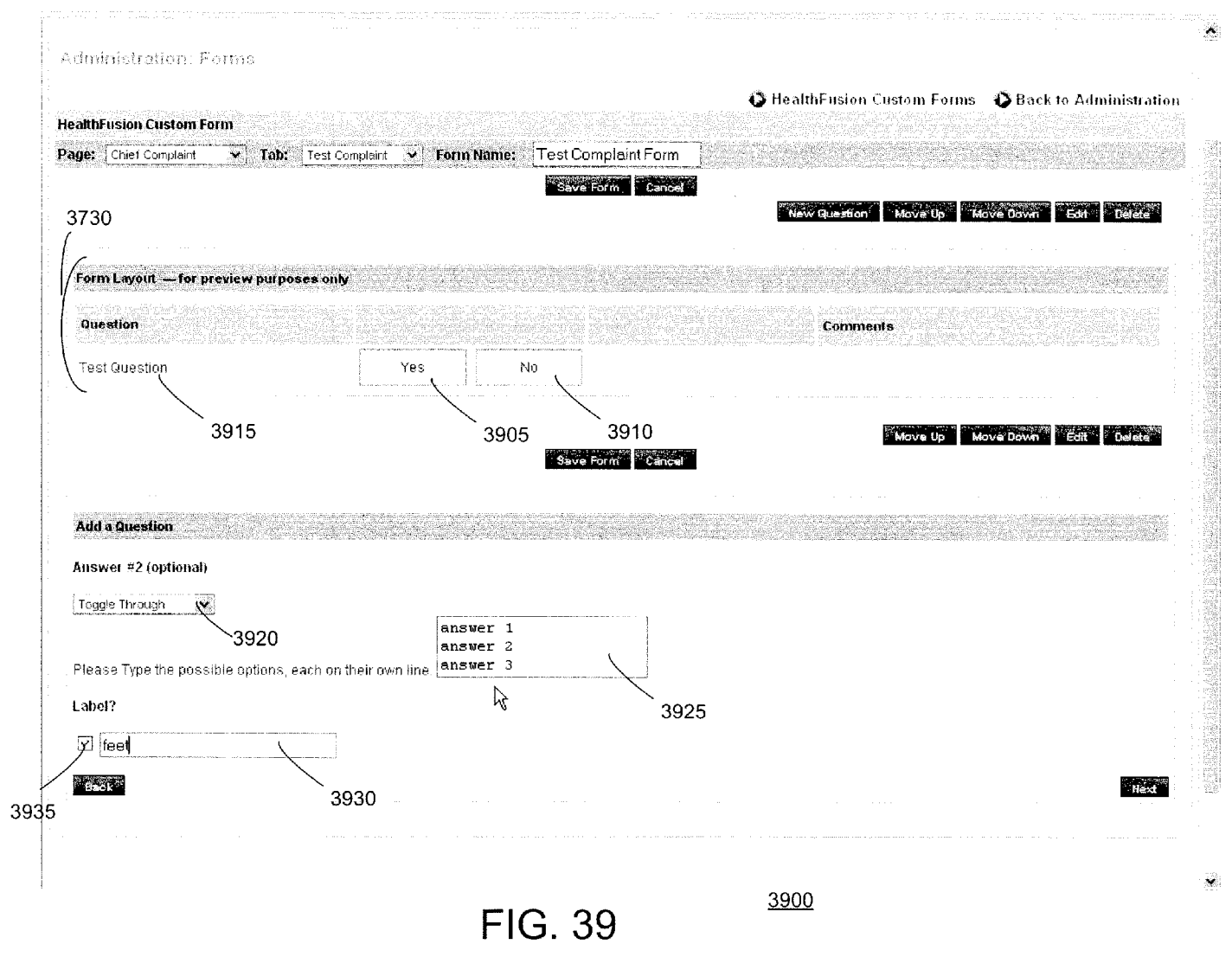

FIG. 39 is a representative screen display 3900 showing the question having a yes/no first answer type in the form layout section 3730. Because the answer type is yes/no, a yes button 3905 and a no button 3910 are displayed next to the text of the question 3915. Different answer types would result in different user interface components to collect an answer of a particular type. For instance, a date answer type may include a calendar component for selecting a date or a text answer type may include a text box.

Questions may also be associated with an optional second answer type. A drop down list 3920 may be used to select the second answer type. Possible second answer types include all available types for the first answer type, as well as the option to indicate that there is no second answer type. A second answer type of toggle through is shown as selected in the drop down list 3920. For a toggle through answer type, two or more possible options may be input into a text box 3925. The first option listed may be used as the default option that is initially selected. Alternatively, any other value may be chosen as the default value for the toggle through answer type. Optionally, a toggle through option may include a label, which may be entered in a text box 3930. A check box 3935 may be used to indicate if the label is to be displayed.

Figure 40:
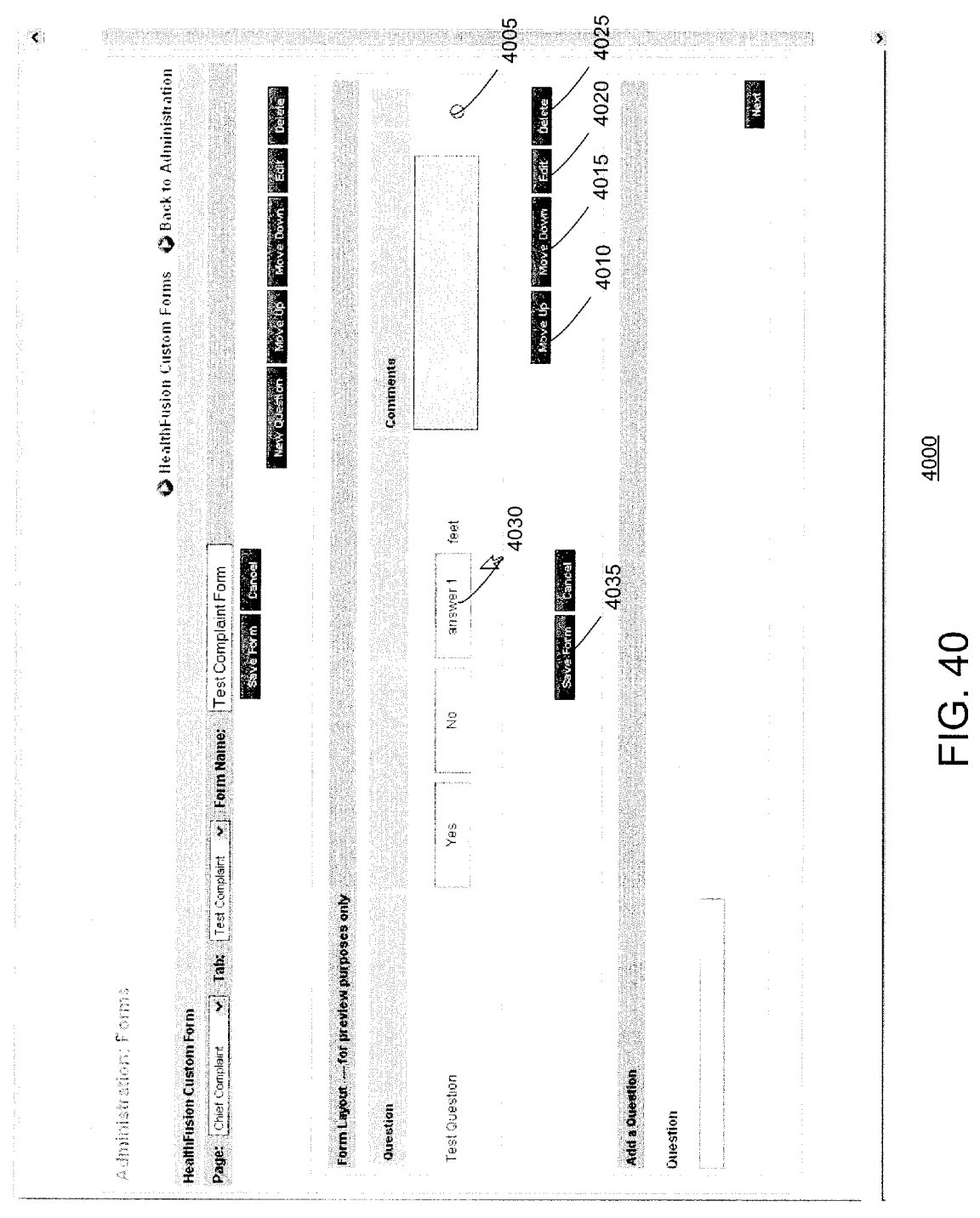

FIG. 40 is a representative screen display 4000 showing the question having a yes/no first answer type and a toggle through second answer type in the form layout section 3730. The second answer type of the question is toggle through that has three options: answer 1, answer 2, and answer 3. Accordingly, a button 4130 whose text is a default option answer 1 is shown. Activating the button 4030 causes the next option to be chosen and the text of the button 4030 to change to answer 2. Activating the button 4030 again selects answer 3 and the text of the button 4030 changes accordingly. As answer 3 is the last option for this particular answer type, activating the button 4030 again would cause the first answer 1 option to be selected. Thus, the button 4030 allows toggling through the three various options. A save button 4035 saves the form.

A form may be associated with numerous questions. A radio button 4005 may be used to select the question. The selected question may now be edited, deleted, or its position in the form changed. A move up button 4000 may be used to move the question up one position in the form. Similarly, a move down button 4015 may be used to move the question down one position in the form. An edit button 4020 may be used to change the text of the question, the first answer type, the second answer type, or the label of the second answer. Additionally, a delete button 4025 may be used to remove the question from the form.

The screen display 3300 is an example of a complete custom form with multiple questions for collecting patient data related to a sore throat. In addition to an answer, each question also has a corresponding notes field for associating text with the question. As described above, a question may allow multiple answers. A second answer may be enabled based upon a first answer. For instance, a question 3310 has a yes/no first answer type and a toggle through second answer type. If a no button 3315 is selected, there is no need to collect a patient's temperature. Accordingly, the toggle through button 3320 may be disabled. The toggle through button 3320 would be enabled when a yes button 3325 is selected to indicate that the patient has a fever. Once all of the patient data is collected, the custom form and the collected answers and notes may be saved to a storage device. The custom form and the collected answers may also be integrated into the patient's electronic chart. Additional questions, answer types, or answers may be added or edited to further customize the custom form based upon continual experience of the medical professional. Seldom-used questions may also be deleted. Customized forms allow a medical professional to record patient data quickly and accurately, while allowing the medical professional to spend more time focusing on the patient.

Once all relative data relating to the patient examination is entered in the electronic health record application, an examination summary can be generated. FIGS. 32A, 32B, 32C, and 32D are representative screen displays 3200a-d of an examination summary. The examination summary includes various portions, which displays patient data from the examination. In addition, the examination summary may include data from the patient management application and the claims management system. One portion of the examination summary is a medical history portion 3225 that displays data that was collected as described with reference to FIG. 12. The vital sign data that was collected as described with reference to FIG. 13 is displayed in a vital signs portion 3230. The examination summary can also incorporate various outputs from the examination module in whole. For example, the physical examination summary as described with reference to FIG. 22 is integrated into a portion 3240 of the examination summary. The physical examination summary includes text 3245 which is generated based upon touch phrase button 2105 and the additional data associated with the touch phrase button 2105. The examination summary also contains portions relating to coding data 3255 as described with reference to FIG. 24; prescription data 3260 as described with reference to FIG. 26; osteopathic data 3270 as described with reference to FIG. 31; follow-up data 3275 as described with reference to FIG. 28; and care plan data 3280 as described with reference to FIG. 29.

The examination summary is not limited to summarizing data collected during the patient's examination. For instance, a problem list 3285 lists problems that were entered in the examination as described with reference to FIG. 23. The problem list 3285 also includes problems that were recorded as part of an earlier examination. Earlier examination data may be retrieved from the patient management application, or the computer 105 or the database 110 of the health management system. The examination summary can be incorporated into a patient's electronic health record. Integrating the examination summary into the patient's electronic health record allows the medical professional to update the electronic health record without having to re-input the data collected during the examination.

It should be appreciated, of course, that the details associated with the product described herein merely represent one possible implementation. Representative embodiments are described herein with reference to drawings. These drawings illustrate certain details of specific embodiments that implement the systems and methods and programs of the representative embodiments. However, describing the representative embodiments with drawings should not be construed as imposing on the claims any limitations that may be present in the drawings. The representative embodiments contemplate methods, systems and program products on any machine-readable media for accomplishing its operations. The representative embodiments may be implemented using an existing computer processor, or by a special purpose computer processor incorporated for this or another purpose or by a hardwired system.

Embodiments may include program products comprising machine-readable media for carrying or having machine-executable instructions or data structures stored thereon. Such machine-readable media can be any available media which can be accessed by a general purpose or special purpose computer or other machine with a processor. By way of example, such machine-readable media can include RAM, ROM, EPROM, EPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired and wireless) to a machine, the machine properly views the connection as a machine-readable medium. Thus, any such connection is properly termed machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Embodiments are described in the general context of method operations which may be implemented in one embodiment by a program product including machine-executable instructions, such as program code, for example in the form of program modules executed by machines in networked environments. Generally, program modules include routines, programs, objects, components, data structures, etc. that perform particular tasks or implement particular abstract data types. Machine-executable instructions, associated data structures, and program modules represent examples of program code for executing steps of the methods described herein. The particular sequence of such executable instructions or associated data structures represents an example of corresponding acts for implementing the functions described in such operations.

Embodiments may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet, and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments may also be practiced in distributed computing environments where tasks are performed by local and remote processing devices that are linked (either by hardwired links, wireless links or by a combination of hardwired and wireless links) through a communications network. In a distributed computing environment, program modules may be located in both local and remote memory storage devices.

It should be noted that although the flow charts provided herein show a specific order of method operations, it is understood that the order of these operations may differ from what is depicted. Also, two or more operations may be performed concurrently or with partial concurrence. Such variation will depend on the software and hardware systems chosen and on designer choice. Likewise, software and web implementations of the representative embodiments could be accomplished with standard programming techniques with rule based logic and logic to accomplish the various database searching steps, correlation steps, comparison steps and decision steps. It should also be noted that the word "component" as used herein and in the claims is intended to encompass implementations using one or more lines of software code, and/or hardware implementations, and/or equipment for receiving manual inputs.

The foregoing description of representative embodiments has been presented for purposes of illustration and description. It is not intended to be exhaustive or to limit the present claims to the precise form disclosed, and modifications and variations are possible in light of the above teachings or may be acquired from practice of the representative embodiments. The representative embodiments were chosen and described in order to explain the principles of the present claims and their practical application to enable one skilled in the art to utilize the present claims in various embodiments and with various modifications as are suited to the particular use contemplated.

What is claimed is:

1. A method comprising:
   initializing a touch phrase button by a processor, wherein the initializing comprises associating a first text with the touch phrase button;
   receiving an input associated with the touch phrase button;
   updating, by the processor, a state of the touch phrase button from a non-save state to a save state in response to the input without receiving a second input, wherein updating the state of the touch phrase button comprises automatically associating a second text with the touch phrase button without user input of the second text, wherein the second text is displayed within the touch phrase button; and
   communicating the state of the touch phrase button to a memory device, wherein the communicating the state of the touch phrase button occurs automatically in response to the state of the touch phrase button being a save state.

2. The method of claim 1, wherein the second text is configured for compilation in a medical chart.

3. The method of claim 1 further comprising:
   receiving note data associated with the touch phrase button.

4. The method of claim 1 further comprising:
   initializing a second touch phrase button, wherein the initializing comprises associating a third text with the second touch phrase button, and wherein the third text is configured for compilation in a report;
   receiving a second input associated with the second touch phrase button; and
   updating a state of the touch phrase button based upon the second input, wherein updating the state of the second touch phrase button comprises associating a fourth text with the second touch phrase button, and wherein the fourth text is configured for compilation in a report.

5. The method of claim 1 further comprising:
   receiving text associated with a custom question;
   receiving a first answer type associated with the custom question;

receiving a second answer type associated with the custom question;

displaying the text associated with the custom question;

receiving a first answer corresponding to the first answer type; and receiving a second answer corresponding to the second answer type.

6. The method of claim 5, wherein the first answer type comprises a yes or no type response, a number type response, a text type response, a date type response, a select list type response, a toggle through type response, or a multiple select list type response;

the second answer type comprises a yes or no type response, a number type response, a text type response, a date type response, a select list type response, a toggle through type response, or a multiple select list type response; and the first answer type is different from the second answer type.

7. The method of claim 1, wherein the second text is displayed within the touch phrase button in place of the first text.

8. The method of claim 1, wherein updating the state of the touch phrase button further comprises changing an appearance of the touch phrase button.

9. The method of claim 8, wherein the changing the appearance of the touch phrase button comprises changing an icon, a font, or text formatting of the touch phrase button.

10. The method of claim 1, wherein the updating the state of the touch phrase button changes the state of the touch phrase button from a non-save state to the save state.

11. An apparatus comprising:
a user interface configured to:
present a touch phrase button;
receive an input associated with the touch phrase button; and
a processor configured to:
initialize the touch phrase button, wherein the initializing comprises associating a first text with the touch phrase button;
update a state of the touch phrase button from a non-save state to a save state in response to the received input without receiving a second input, wherein updating the state of the touch phrase button comprises automatically associating a second text with the touch phrase button without user input of the second text, wherein the second text is displayed within the touch phrase button; and
communicate the state of the touch phrase button to a memory device, wherein the state of the touch phrase button is communicated automatically in response to the state of the touch phrase button being a save state.

12. The apparatus of claim 11, wherein the second text is configured for compilation in a medical chart.

13. The apparatus of claim 11, wherein the processor is further configured to:
receive note data associated with the touch phrase button.

14. The apparatus of claim 11, wherein the processor is further configured to:
initialize a second touch phrase button, wherein the initializing comprises associating a third text with the second touch phrase button, and wherein the third text is configured for compilation in a report;
receive a second input associated with the second touch phrase button; and
update a state of the touch phrase button based upon the second input, wherein updating the state of the second touch phrase button comprises associating a fourth text with the second touch phrase button, and wherein the fourth text is configure for compilation in a report.

15. The apparatus of claim 11 wherein the processor is further configure to:
receive text associated with a custom question;
receive a first answer type associated with the custom question;
receive a second answer type associated with the custom question;
display the text associated with the custom question;
receive a first answer corresponding to the first answer type; and
receive a second answer corresponding to the second answer type.

16. An article of manufacture including a non-transitory computer-readable medium having instructions stored thereon that, if executed by a computing device, cause the computing device to perform operations comprising:
initializing a touch phrase button by a processor, wherein the initializing comprises associating a first text with the touch phrase button;
receiving an input associated with the touch phrase button;
updating a state of the touch phrase button from a non-save state to a save state in response to the input without receiving a second input, wherein updating the state of the touch phrase button comprises automatically associating a second text with the touch phrase button without user input of the second text, wherein the second text is displayed within the touch phrase button; and
communicating the state of the touch phrase button to a memory device, wherein the communicating the state of the touch phrase button occurs automatically in response to the state of the touch phrase button being a save state.

17. The article of manufacture of claim 16, wherein the second text is configured for compilation in a medical chart.

18. The article of manufacture of claim 16, wherein the instructions, if executed by the computer device, cause the computing device to further perform operations comprising:
receiving note data associated with the touch phrase button; and
receiving additional data associated with the touch phrase button.

19. The article of manufacture of claim 16, wherein the instructions, if executed by the computer device, cause the computing device to further perform operations comprising:
initializing a second touch phrase button, wherein the initializing comprises associating a third text with the second touch phrase button, and wherein the third text is configured for compilation in a report;
receiving a input associated with the second touch phrase button; and
updating a state of the touch phrase button based upon the input associated with the second touch phrase button, wherein updating the state of the second touch phrase button comprises associating a fourth text with the second touch phrase button, and wherein the fourth text is configure for compilation in a report.

20. The article of manufacture of claim 16, wherein the instructions, if executed by the computer device, cause the computing device to further perform operations comprising:
receiving text associated with a custom question;
receiving a first answer type associated with the custom question;
receiving a second answer type associated with the custom question;
displaying the text associated with the custom question;

receiving a first answer corresponding to the first answer type; and receiving a second answer corresponding to the second answer type.

* * * * *